(12) United States Patent
Kanetaka et al.

(10) Patent No.: US 11,066,733 B2
(45) Date of Patent: Jul. 20, 2021

(54) CALCIUM-BASED METALLIC GLASS ALLOY MOLDED BODY FOR MEDICAL USE AND PRODUCTION METHOD THEREOF

(71) Applicant: TOHOKU UNIVERSITY, Sendai (JP)

(72) Inventors: Hiroyasu Kanetaka, Sendai (JP); Guoqiang Xie, Sendai (JP); Hajime Takada, Sendai (JP)

(73) Assignee: TOHOKU UNIVERSITY, Sendai (JP)

(*) Notice: Subject to any disclaimer, the term of this patent is extended or adjusted under 35 U.S.C. 154(b) by 0 days.

(21) Appl. No.: 16/089,267

(22) PCT Filed: Mar. 30, 2017

(86) PCT No.: PCT/JP2017/013469
§ 371 (c)(1),
(2) Date: Sep. 27, 2018

(87) PCT Pub. No.: WO2017/170964
PCT Pub. Date: Oct. 5, 2017

(65) Prior Publication Data
US 2019/0024223 A1 Jan. 24, 2019

(30) Foreign Application Priority Data
Mar. 31, 2016 (JP) ............... JP2016-071145

(51) Int. Cl.
*B22F 3/14* (2006.01)
*A61L 29/02* (2006.01)
*A61L 29/14* (2006.01)
*A61L 31/02* (2006.01)
*A61L 31/14* (2006.01)
*B22F 1/00* (2006.01)
*B22F 9/08* (2006.01)
(Continued)

(52) U.S. Cl.
CPC ............ *C22C 45/00* (2013.01); *A61L 31/022* (2013.01); *A61L 31/026* (2013.01); *A61L 31/14* (2013.01);
(Continued)

(58) Field of Classification Search
CPC ....... C22C 45/00; C22C 1/04; C22C 2200/02; C22C 1/0408; C22C 1/02; C22C 1/00;
(Continued)

(56) References Cited

U.S. PATENT DOCUMENTS
2014/0348571 A1* 11/2014 Prest ................... B21J 5/04
403/52

FOREIGN PATENT DOCUMENTS
CN 102766829 A * 11/2012
CN 102766829 A    11/2012
(Continued)

OTHER PUBLICATIONS

"Biodegradable CaMgZn bulk metallic glass for potential skeletal application", Wang et al., Acta Biomaterialia, vol. 7, May 1, 2011, pp. 3196-3208 (Wang) (Year: 2011).*
(Continued)

*Primary Examiner* — Daniel J. Schleis
*Assistant Examiner* — Kevin C T Li
(74) *Attorney, Agent, or Firm* — Procopio, Cory, Hargreaves & Savitch LLP

(57) ABSTRACT

It is an object of the present invention to provide a production method of a calcium-based metallic glass alloy molded body for medical use which has a biodegradable property, has a mechanical strength equal to or higher than that of metal materials, and enables complex molding and a wide range of applications. The calcium-based metallic glass alloy molded body for medical use is produced by mixing a metal powder including a calcium powder, alloying the mixed metal powder, and sintering the alloyed mixed metal powder.

22 Claims, 15 Drawing Sheets

(51) Int. Cl.
| | |
|---|---|
| *C22C 1/00* | (2006.01) |
| *C22C 1/04* | (2006.01) |
| *C22C 24/00* | (2006.01) |
| *C22C 45/00* | (2006.01) |
| *C22C 1/02* | (2006.01) |
| *B22F 3/105* | (2006.01) |
| *B22F 3/24* | (2006.01) |

(52) U.S. Cl.
CPC .............. *B22F 3/105* (2013.01); *B22F 3/24* (2013.01); *B22F 9/082* (2013.01); *C22C 1/00* (2013.01); *C22C 1/02* (2013.01); *C22C 1/04* (2013.01); *C22C 1/0408* (2013.01); *C22C 24/00* (2013.01); *B22F 2003/1051* (2013.01); *B22F 2003/247* (2013.01); *B22F 2998/10* (2013.01); *B22F 2999/00* (2013.01); *C22C 2200/02* (2013.01)

(58) Field of Classification Search
CPC .. C22C 24/00; B22F 9/082; B22F 3/24; B22F 3/105; B22F 2003/247; B22F 2003/1051; B22F 2999/00; B22F 2998/10; A61L 31/022; A61L 31/14; A61L 31/026
See application file for complete search history.

(56) References Cited

FOREIGN PATENT DOCUMENTS

| JP | 2015-096474 A | | 5/2015 |
|---|---|---|---|
| JP | 2015096474 A | * | 5/2015 |
| JP | 2016-194095 A | | 11/2016 |

OTHER PUBLICATIONS

"Formation of Ca—Mg—Zn bulk glassy alloy by casting into cone-shaped copper mold", Park et al., J. Mater. Res., vol. 19, No. 3, Mar. 2004, pp. 685-688 (Park) (Year: 2004).*

"Fabrication of porous Zr—Cu—Al—Ni bulk metallic glass by spark plasma sintering process", Xie et al., Scripts Materialia, vol. 55, Issue 8, Oct. 2006, pp. 687-690 (Xie) (Year: 2006).*
International Search Report for related International Application No. PCT/JP2017/013469, dated Jul. 4, 2017; English translation provided.
Written Opinion of the International Searching Authority for related International Application No. PCT/JP2017/013469, dated Jul. 4, 2017; English translation provided.
International Preliminary Report on Patentability for related International Application No. PCT/JP2017/013469, dated Dec. 19, 2017; English translation provided.
Yamamoto, A. et al. "Biomedical application of magnesium alloys" Journal of Japan Institute of Light Metals, 2008, 20 pages, vol. 58, No. 11; English translation provided.
Peuster, M. et al. "A novel approach to temporary stenting: degradable cardiovascular stents produced from corrodible metal-results 6-18 months after implantation into New Zealand white rabbits" Heart, Nov. 1, 2011, 7 pages, vol. 86.
Ueno, A. et al. "High-cycle and Highly Impact Durable Polylactic Acid Resin Molding Compound" Panasonic Electric Works Technical Report, 12 pages, vol. 59, No. 1; English translation provided.
Wang, Y.B. et al. "Biodegradable CaMgZn bulk metallic glass for potential skeletal application" Acta Biomaterialia, May 1, 2011, 13 pages, vol. 7.
Cao, J.D., et al. "Ca—Mg—Zn bulk metallic glasses as bioresorbable metals" Acta Biomaterialia, Mar. 9, 2012, 9 pages, vol. 8.
Jiao, W. et al. "Zinc-based bulk metallic glasses" Journal of Non-Crystalline Solids, Aug. 7, 2010, 4 pages, vol. 356.
Li, H. et al. "Biodegradable Mg—Zn—Ca—Sr bulk metallic glasses with enhanced corrosion performance for biomedical applications" Materials & Design, Nov. 6, 2014, 11 pages, vol. 67.
Notice of Reasons for Refusal for related JP App No. 2018-509486 dated Jan. 5, 2021, 13 pgs.
Park, E.S., et al., Ca—Mg—Zn Bulk Metallic Glasses with Strong Glass-Forming Ability Synthesized Under Air Atmosphere, Journal of Metastable and Nanocrystalline Materials, 2005, vols. 24-25, pp. 687-690.

* cited by examiner

CALCIUM-BASED METALLIC GLASS ALLOY MOLDED BODY FOR MEDICAL USE AND PRODUCTION METHOD THEREOF

CROSS-REFERENCE TO RELATED APPLICATIONS

This application is a U.S. National Stage entry of PCT Application No: PCT/JP2017/013469 filed Mar. 30, 2017, which claims priority to Japanese Patent Application No. 2016-071145, filed Mar. 31, 2016, the contents of which are incorporated herein by reference.

TECHNICAL FIELD

The present invention relates to a calcium-based metallic glass alloy molded body having a biodegradable property and to a production method thereof.

BACKGROUND ART

With the aging of society, the development of biomaterials for medical use that are gentle and safe for living organisms is needed in the medical field. Among them, medical biomaterials such as intraluminal stents, fracture fixation plates, and sutures used for treatment of intraluminal narrowed parts such as blood vessels and esophagus are required to have a property of being absorbed by living bodies after the treatment. Where these materials are not absorbed by the living body, re-operation to remove the material after the treatment becomes necessary, causing problems of invasive risk and secondary infection risk.

Various substances have been studied as raw materials for medical materials having a biodegradable property.

For example, NPL 1 indicates that magnesium having a biodegradable property among metal materials has been studied as a medical material.

However, magnesium has high activity and there is also a problem that the degradation speed in vivo is too fast. Accordingly, it is known that when magnesium itself is used as a raw material in the form of a plate, a large amount of gas is generated subcutaneously thereby forming a cavity.

As for iron, a pure iron stent has been made and the results of implantation into a rabbit blood vessel have been reported (see NPL 1 and 2). However, there is a problem that iron degradation speed in vivo is too slow. Accordingly, it has been indicated that iron embedded as a medical material in a living body remains for a long time as a foreign matter in the living body even after the treatment, the material corrodes, and inflammation occurs in the surroundings.

Furthermore, it is known that polymeric materials such as polylactic acid are low in mechanical strength and inferior in workability, and therefore cannot replace metal materials such as titanium (see NPL 3 and the like). However, despite these properties, polymer materials are superior to other alternative materials in terms of absorptivity in the living body and there is no need for reoperation to remove the polymeric material after the treatment as indicated hereinabove. For this reason, polymeric materials such as polylactic acid are considered promising biomaterials, actual clinical trials thereof have been advanced, and polymeric materials have found application to bone fragment fixing plates, bone screws, absorbable stents, and the like.

Meanwhile, calcium-based metallic glass alloys have recently attracted attention as materials capable of solving all of the above-mentioned problems at the same time. However, it is known that a calcium-based metallic glass alloy produced by a conventional casting method crystallizes as the size thereof increases, so that the alloy does not have metal glass properties unless the thickness thereof is 10 mm or less (see NPL 4 to 6). In other words, a production method suitable for a medical material of a calcium-based metallic glass alloy which is required to have a large size has not yet been established, and accelerated development of a calcium-based metallic glass alloy material for medical use and a production method thereof is desired.

CITATION LIST

Non Patent Literature

[NPL 1] Akiko Yamamoto: "Biomedical Application of Magnesium Alloys", Journal of Japan Institute of Light Metals, 58 (11), 2008, pp. 570-576
[NPL 2] M. Peuster et al.: Heart, 86, 2001, pp. 563-569
[NPL 3] Akira Ueno, Hiroshi Yamamoto, Eiichiro Saito, Yoshihisa Ueda: "High-cycle and Highly Impact Durable Polylactic Acid Resin Molding Compound", Panasonic Electric Works Technical Report, Vol. 59, No. 1, pp. 55-59
[NPL 4] Y. B. Wang et al.: Biodegradable CaMgZn bulk metallic glass for potential skeletal application, Acta Biomaterialia 7 (2011), pp. 3196-3208
[NPL 5] J. D. Cao et al.: Ca—Mg—Zn bulk metallic glasses as bioresorbable metals, Acta Biomaterialia 8 (2012), pp. 2375-2383
[NPL 6] W. Jiao et al.: Zinc-based bulk metallic glasses, Journal of Non-Crystalline Solids 356 (2010), pp. 1867-1870

SUMMARY OF INVENTION

Technical Problem

It is an object of the present invention to provide a calcium-based metallic glass alloy molded body for medical use which has a suitable biodegradable property, has a mechanical strength equal to or higher than that of metal materials, enables complex molding, and can be used for members having large area and thickness; and also to provide a production method thereof.

Solution to Problem

As a result of intensive investigations aimed to achieve the abovementioned object, the inventors of the present invention have found a calcium-based metallic glass alloy molded body for medical use which starts to be gradually absorbed by a living body immediately after implantation therein, eventually decomposes in the living body, and has the same mechanical strength and hardness as metal materials, and have also found a production method thereof.

Thus, the calcium-based metallic glass alloy molded body for medical use can be produced by mixing a metal powder including a calcium powder, alloying the mixed powder, and sintering the alloyed mixed metal powder.

The calcium-based metallic glass alloy molded body for medical use can also be produced by mixing a metal powder including a calcium powder, alloying the mixed powder, dispersing iron crystal grains in the alloyed mixed metal powder, and sintering the alloyed mixed metal powder in which the iron crystal grains have been dispersed.

Advantageous Effects of Invention

When the calcium-based metallic glass alloy produced according to the present invention is used as a raw material for a biomaterial for medical use, since this alloy has mechanical strength and hardness equivalent to those of metal materials, materials for medical use which have a complex shape can be molded, the alloy can be used for members to which pressure is applied due to the structure of the biomaterial or implantation position, and the range of use of calcium-based metallic glass alloy biomaterials is expanded. In addition, gradual absorption of the alloy by the living body starts immediately after the implantation in the living body and the alloy is eventually decomposed in the living body. As a result, not only the removal operation after the treatment is unnecessary, but also the degradation speed can be controlled immediately after the implantation. Furthermore, the production method of the calcium-based metallic glass alloy molded body of the present invention can be adapted to bulk production and can be applied to biomaterials having large size.

DESCRIPTION OF EMBODIMENTS

Figure 1:
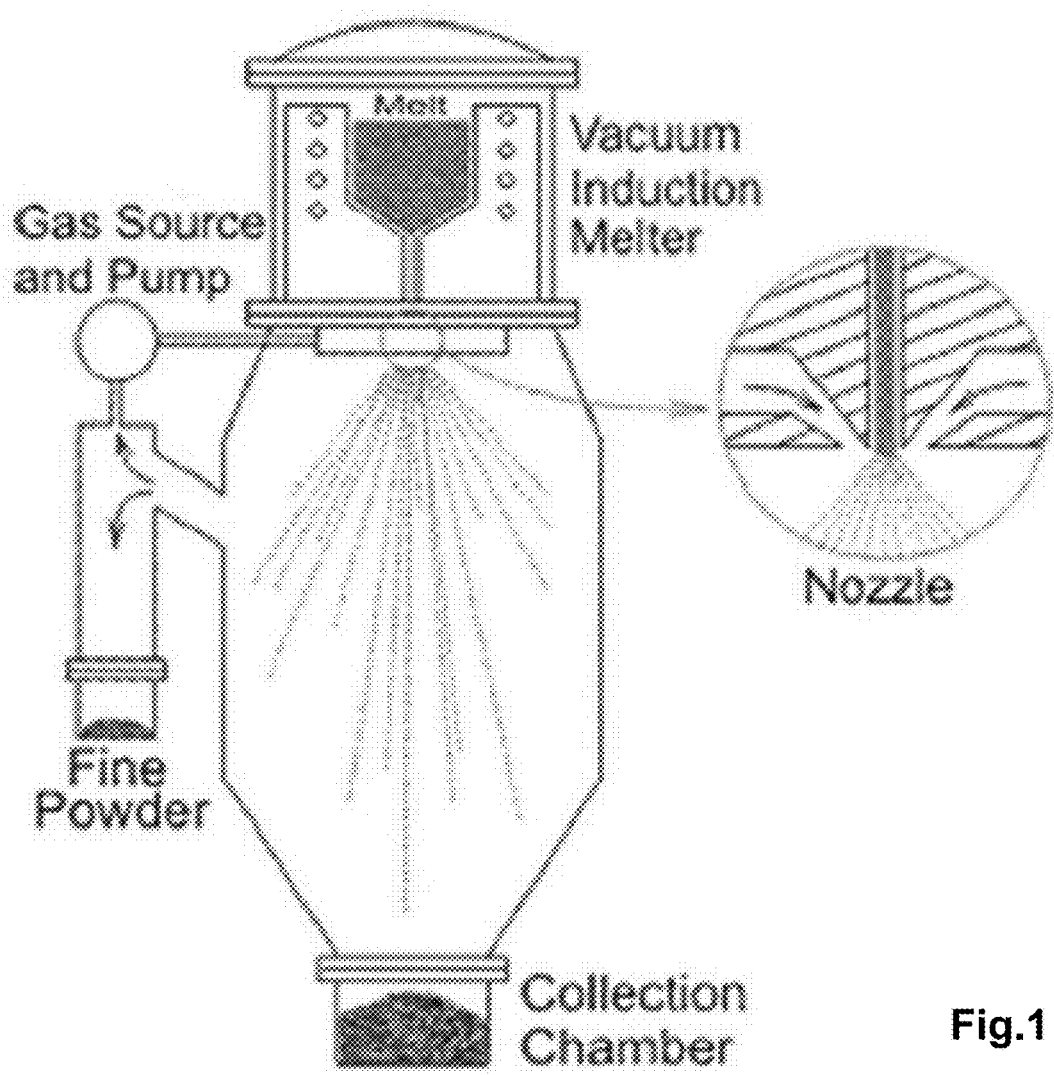
FIG. 1 depicts a device and a conceptual diagram for making a calcium-based metallic glass alloy powder by a gas atomization method.

Prior to the description of embodiments of the invention, the terms used will be clarified. In the present specification, a specimen obtained by mixing metal powders is referred to as "mixed metal powder", a specimen obtained by alloying the mixed metal powder to obtain a metal glass is referred to as "metallic glass alloy powder", a specimen obtained by sintering the metallic glass alloy powder is referred to as "metallic glass alloy", a sintered body of the metallic glass alloy powder is referred to as "metallic glass alloy molded body", and a biomaterial cut out by machining the metallic glass alloy molded body is referred to as "metallic glass alloy biomaterial".

The metal glass, as referred to herein, is a material which is obtained by rapidly cooling from a liquid state and which exhibits glass transition among amorphous alloys. Even when the mixed metal powder is alloyed, the alloy may or may not have properties of a metal glass depending on alloying conditions.

The calcium-based metallic glass alloy molded body for medical use of the present invention is composed of a calcium-based metallic glass alloy including calcium as a main component and includes a region inside the molded body in which the shortest distance from all parts of the surface of the molded body is more than 5 mm.

Further, the production method of a calcium-based metallic glass alloy molded body for medical use of the present invention includes a step of mixing a metal powder including a calcium powder, a step of alloying the mixed metal powder, and a step of sintering the alloyed mixed metal powder.

The calcium powder and the metal powder may be for any applications such as industry, synthetic reagents, agriculture, food, medicine, and the powders are selected from the viewpoints of purity and contained impurities depending on the intended use of the alloy to be produced. When the alloy is to be used for a biomaterial for medical use which has a biodegradable property, it is particularly preferable to select the powders having a purity of 99% or more for medical use in order to ensure biological safety. The particle size is preferably 50 mesh to 200 mesh which facilitates treatment in the step of alloying by a solid phase reaction utilizing mechanical energy.

In the mixed metal powder of the present invention, other metals such as magnesium and zinc may be included in addition to calcium.

Further, a trace amount of a metal powder which is usually added to a material to be used in an alloy to be produced may be added to the calcium powder, the magnesium powder, and the zinc powder.

The calcium powder and the other metal powders are mixed at a mass ratio corresponding to the molar ratio of each component constituting the metallic glass alloy powder to be made.

The mass ratio is such that the alloy can be theoretically made when the amount of the calcium powder exceeds zero and is less than 100 at. %, with the total of the metal powders being not more than a total of 100 at. % of the total powder amount. However, from the viewpoints of the biodegradable property and material processability, a $Ca_xMg_yZn_z$ metallic glass alloy with x=40 at. % to 70 at. %, y=0 at. % to 30 at. %, z=0 at. % to 35 at. % is preferred. It has been confirmed that where these ranges are exceeded, the alloy may not have the properties of metal glass in some cases.

The calcium-based metallic glass alloy molded body for medical use of the present invention may have any shape in addition to a bulk shape such as a columnar shape, a prismatic shape, a spherical shape, a rod shape, a plate shape, and a conical shape.

The thickness of the molded body is not particularly limited, and properties of a metallic glass alloy are demonstrated whether the molded body is thin or thick. Therefore, the molded body can have a shape such that includes a region inside the molded body in which the shortest distance from all parts of the surface of the molded body is more than 5 mm, or 6 mm or more, or 7.5 mm or more. That is, it can be said that the molded body of the present invention has the properties of metal glass even when the molded body has a thickness of more than 10 mm, or 12 mm or more, or 15 mm or more.

The calcium-based metallic glass alloy molded body for medical use may be machined (cut, ground, polished, and the like) to an arbitrary shape of a biomaterial such as a shape of a predetermined bone, a shape of a screw, a shape of an implant, a shape of a covering material, a shape of a fixing plate, and the like, and can be used as a calcium-based metallic glass alloy biomaterial for medical use.

In the step of alloying the mixed metal powder, it is possible to use a gas atomization method, a casting method, a mechanical alloying method, or a method combining a casting method and a mechanical alloying method. In order to generate the metal glass by alloying the mixed metal powder, it is effective to use a gas atomization method, a mechanical alloying method, and a combined method using a mechanical alloying method after treatment by a casting method.

In the gas atomization method, high-purity elemental metals are mixed so as to obtain a composition of a metallic glass alloy and the mixture is melted in an inert gas such as Ar purified to a high purity to make a master ingot. Then, a metallic glass alloy powder can be made by remelting the master ingot under reduced pressure and etching with high pressure Ar gas while spraying the melt from a nozzle.

One of the advantages of the gas atomization method over the mechanical alloying method is that it is possible to produce a large amount of metallic glass alloy powder at once. FIG. 1 depicts the outline of a gas atomizing device.

In the mechanical alloying method, a plurality of metal powders is placed in a chamber including a ball and vigorously stirred by rotating the chamber. The plurality of stirred metal powders in the chamber is alloyed by a solid phase reaction at an atomic level.

Figure 2:
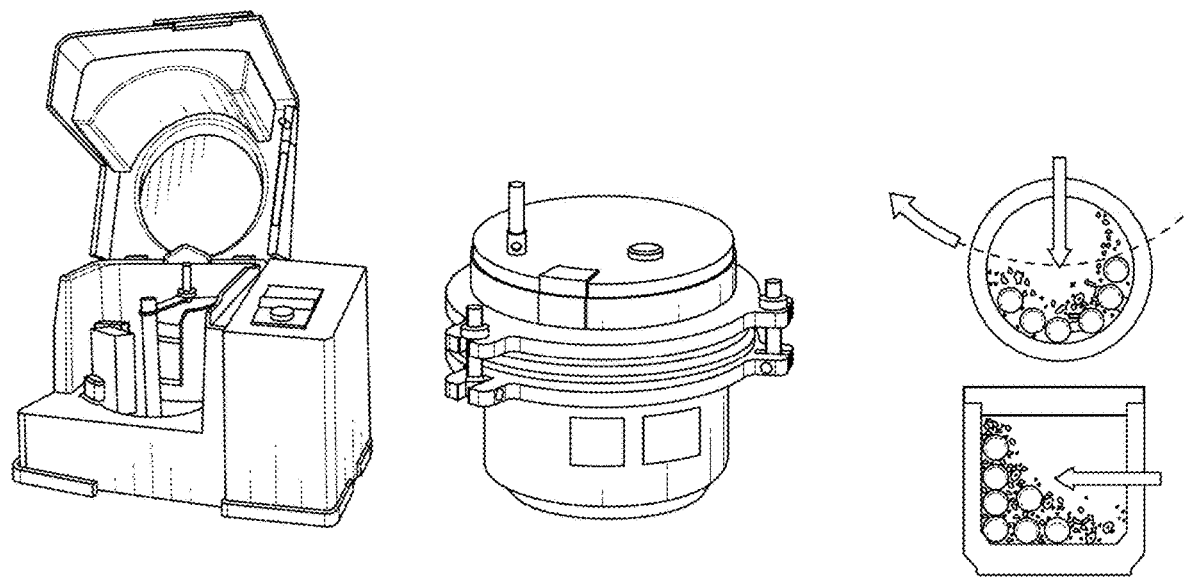
FIG. 2 depicts a device and a conceptual diagram for making a calcium-based metallic glass alloy powder by a mechanical alloying method.

FIG. 2 depicts the appearance of a mechanical alloying device, the image of the chamber, and the conceptual diagram inside the chamber.

The particles of the metallic glass alloy powder made by the mechanical alloying method need to be homogeneous. This is because a homogeneous calcium-based metallic glass alloy molded body can be produced by subjecting the homogeneous alloy powder to the subsequent sintering step. Therefore, the alloying conditions in the mechanical alloying method are set so that the metallic glass alloy powder after the mechanical alloying has a particle size of 150 µm or less.

Specifically, the rotation speed is set to 250 rpm to 650 rpm, the solid phase reaction time is set to 0.5 h to 45 h, the mass ratio of the specimen to the ball is set to 1/100 to 1/1, and the like. The atmosphere in the chamber may be replaced with Ar gas or the like.

The casting method is not particularly limited, and a known method can be used. For example, an alloy ingot of a mixed metal powder can be made by a copper mold casting method using a high-frequency melting furnace, a high frequency induction heating device, a BN crucible, and a copper mold.

It has been confirmed that although the ingot made by the casting method is an alloy, the alloy is unlikely to have the properties of metal glass although it depends on conditions of making.

In the method of using the mechanical alloying method in combination with the casting method, the alloy ingot obtained by the casting method is minutely cut with a nipper or the like and a metallic glass alloy powder is then obtained by the mechanical alloying method.

Whether or not the specimen alloyed by the above methods is a metallic glass alloy powder having the properties of metal glass can be confirmed by measuring an X-ray diffraction spectrum (X-ray diffraction pattern) with an X-ray diffraction (XRD) device.

The measurement conditions of the X-ray diffraction device are set such as to obtain an X-ray diffraction spectrum (X-ray diffraction pattern) showing an X-ray diffraction intensity (arbitrary scale) with respect to a twofold ($2\theta$) incident angle ($\theta$) of X-rays on the specimen. Diffraction peaks of individual metals that have been mixed appear before the alloying step, but as the alloying progresses and the system assumes the properties of metal glass, the diffraction peaks becomes broad and disappear. The alloyed state of the mixed metal powder is confirmed by using such a pattern change of the X-ray diffraction spectrum.

The powder shape and particle size of the alloyed specimen can be confirmed with a scanning electron microscope (SEM) image or the like.

The step of sintering the alloyed mixed metal powder is not particularly limited as long as the properties of metal glass can be maintained, and may be selected according to the purpose from powder metallurgy methods, for example, a reaction sintering method, a normal pressure sintering method, a pressure sintering method, a re-sintering method, a sintering method using plasma, and the like.

The pressure sintering method is a method of sintering a powder specimen under pressure, and such a method can densify a specimen, examples thereof including a hot press method, a gas pressure sintering method, a hot isostatic press sintering method, and the like. The hot press method is a pressure sintering method generally of a uniaxial pressing system in which a powder specimen is filled in a cylindrical mold and compressed by a pair of upper and lower punches.

The sintering methods using plasma include a thermal plasma sintering method, a spark plasma sintering method and the like, and the appropriate method is selected according to the purpose.

The spark plasma sintering method (SPS; Spark Plasma Sintering) is a method of sintering a specimen by mechanical pressurization and pulse current heating. In general, a specimen is sintered by passing a pulse current with an average current value of several thousand amperes through the specimen. The pulse current flows to the powder particle contact parts in the powder specimen and heat generation concentrates at the contact parts to promote neck formation between the powder particles. Therefore, it is a sintering method enabling sintering at low temperature in a short time.

Figure 3:
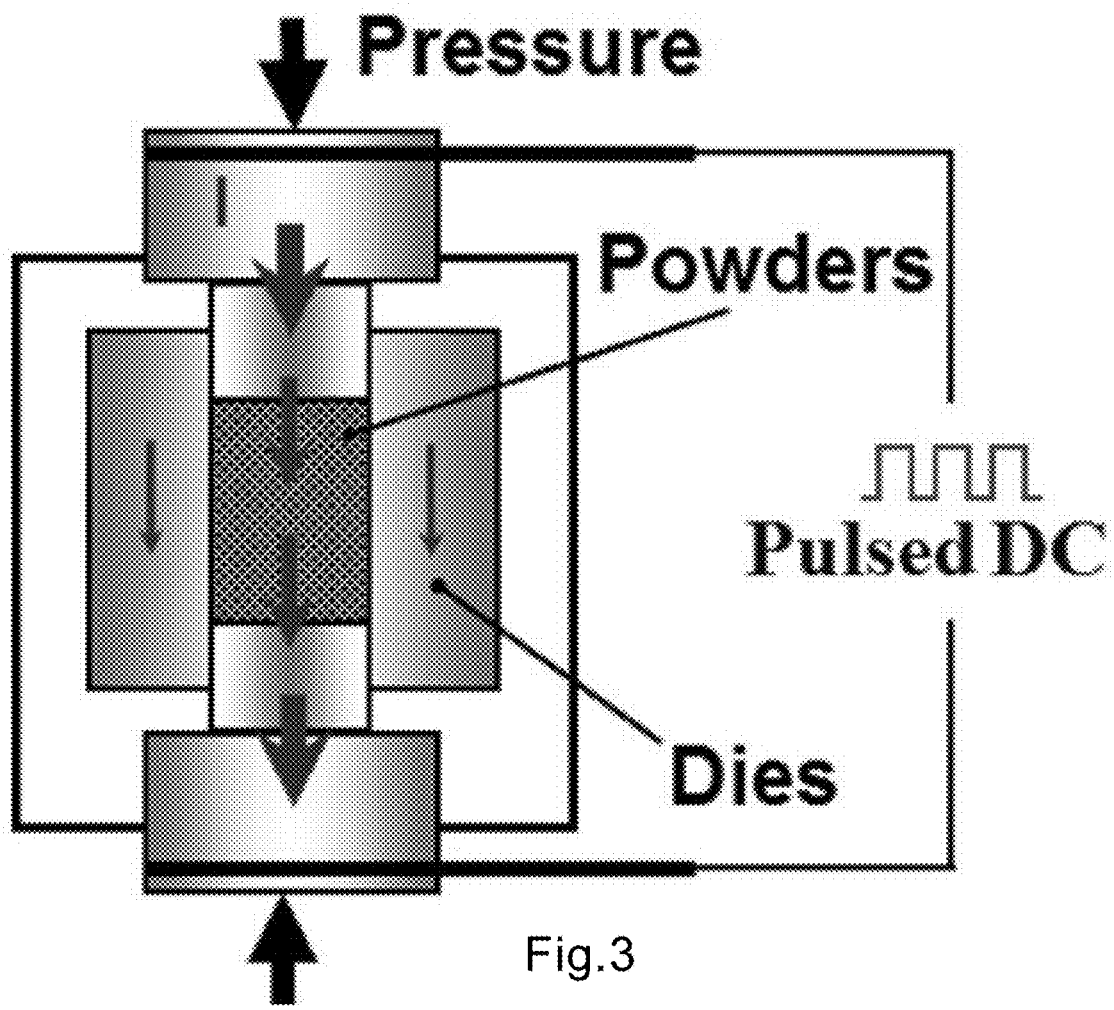
FIG. 3 depicts a conceptual diagram of a device used in a spark plasma sintering method.

FIG. 3 depicts the outline of a device used in the spark plasma sintering method.

The sintered body made by the spark plasma sintering method, that is, the metallic glass alloy molded body in the present invention is required to have mechanical properties and strength suitable for the intended use of the material, to have homogeneity, and to show little changes in microstructure caused by sintering, that is, the metal glass is required not to crystallize. Therefore, the sintering conditions in the spark plasma sintering method are set such that the sintered metallic glass alloy molded body has mechanical properties and strength suitable for the intended use of the material, has homogeneity, and shows little changes in microstructure caused by sintering.

Figure 4:
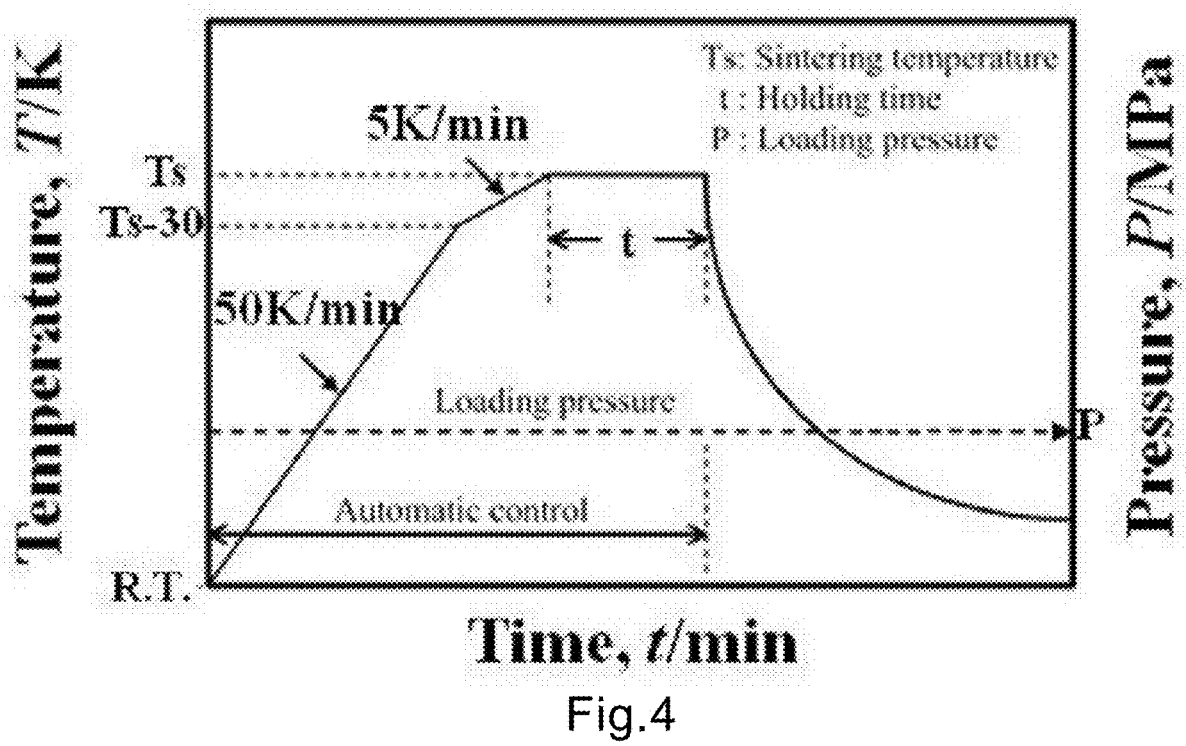
FIG. 4 depicts a temperature and a loading pressure process at the time of making a metallic glass alloy molded body by a spark plasma sintering method.

Specifically, the loading pressure is set to 10 MPa to 800 MPa, the holding time after reaching the sintering temperature is set to 0 min to 20 min, and a sintering temperature is set to 85° C. to 145° C., and the like. An example of the temperature and loading pressure process is depicted in FIG. 4.

In particular, in the present invention, it is important to set the sintering temperature, and it is preferable not to exceed the temperature at which crystallization occurs and to select a temperature as high as possible.

The homogeneity of the sintered body, that is, the metallic glass alloy molded body in the present invention, is also confirmed by a scanning electron microscope (SEM) image, an X-ray diffraction (XRD) device, or the like.

In addition, an X-ray diffraction (XRD) device or the like can be used to confirm that the metallic glass alloy molded body exhibits glass transition as metal glass.

In the production method of the calcium-based metallic glass alloy molded body for medical use of the present invention, a step of dispersing iron (Fe) crystal grains in a metallic glass alloy powder can be further included between the step of alloying the mixed metal powder including the calcium powder and the step of sintering the alloyed mixed metal powder.

In the step of dispersing the Fe crystal grains, the Fe crystal grains are mixed with the metallic glass alloy powder in an amount of 5 volume % to 30 volume %, more preferably 5 volume % to 25 volume % to make a Fe-dispersed metallic glass alloy powder. A method of mixing the metal glass powder and the Fe crystal grains is not particularly limited as long as the Fe crystal grains can be uniformly dispersed.

The purpose of dispersing the Fe crystal grains is to improve the mechanical strength of the calcium-based metallic glass alloy molded body of the present invention and to enable the control of the degradation speed in vivo. Therefore, where the amount of Fe crystal grains is less than 5 volume %, the improvement of mechanical strength and the control of the degradation speed are insufficient, while where the amount of Fe crystal grains exceeds 30 volume %, the mechanical strength is improved, but the biodegradable property of the calcium-based metallic glass alloy molded body is lowered.

From the viewpoint of uniformly dispersing Fe crystal grains in the metallic glass alloy powder, the Fe crystal grains preferably have a particle size of 2 μm to 200 μm, more preferably 2 μm to 50 μm, and even more preferably 3 μm to 5 μm.

The calcium-based metallic glass alloy molded body produced by the production method of a calcium-based metallic glass alloy molded body for medical use of the present invention is characterized in that the compressive strength thereof, as a mechanical property, is 300 MPa or more, and preferably 320 MPa or more.

The compressive strength as a mechanical property is evaluated by measuring the yield point or the like in the compression test. The yield point is obtained by compressing a quadrangular prism-shaped specimen in the height direction and measuring the strain (%) against the compressive stress (MPa). A phenomenon occurring in general alloys and metals is that strain increases as compressive stress increases from zero, but after a yield point is reached, the stress decreases despite the increase in strain. This phenomenon is used to determine the yield point from a stress-strain diagram.

The calcium-based metallic glass alloy molded body produced by the production method of a calcium-based metallic glass alloy molded body for medical use of the present invention is characterized in that the Vickers hardness is 120 HV or more, and preferably 160 HV or more.

The hardness of the calcium-based metallic glass alloy molded body is measured by a hardness test method for metals or the like. Hardness test methods for metals serve to measure Brinell hardness (BHN), Vickers hardness (VHN), Rockwell hardness, and the like. In these hardness test methods, a steel ball, a diamond pyramid or a conical indenter is pressed against the surface of a sintered body (alloy) to measure the deformation amount thereof.

The test method of Vickers hardness (VHN) is defined by JIS methods (JIS Z 2244, JIS B 7725) and involves pushing a square pyramid diamond indenter into the surface of a specimen (test piece), releasing the test force, and then measuring the diagonal length of the depression remaining on the surface.

The calcium-based metallic glass alloy molded body produced by the production method of a calcium-based metallic glass alloy molded body for medical use of the present invention is characterized in that in an SBF (simulated body fluid) immersion test, a degradation rate in immersion for 3 days is 90 mass % or more, preferably 93 mass % or more.

The degradation rate of the calcium-based metallic glass alloy molded body in the simulated body fluid is measured by the SBF (simulated body fluid) immersion test or the like.

In the SBF immersion test for measuring the degradation rate in immersion for 0 days to 6 days, a calcium-based metallic glass alloy molded body molded in a mold having a diameter of 15 mm is cut and immersed in an SBF, and the decrease in mass of the calcium-based metallic glass alloy molded body is measured on a daily basis to determine the degradation rate. In the SBF immersion test, the mass counted as the mass of the calcium-based metallic glass alloy molded body is that remaining as a solid after sample collapse, that is, all the solids other than those dissolved in SBF as ions.

The SBF has the following composition: NaCl: 8.035 g, NaHCO$_3$: 0.355 g, KCl: 0.225 g, K$_2$HPO$_4$.3H$_2$O: 0.231 g, MgCl$_2$.6H$_2$O: 0.311 g, 1.0M HCl: 39 ml, CaCl$_2$): 0.292 g, NaSO$_4$: 0.072 g, and Tris: 6.118 g.

Further, the calcium-based metallic glass alloy molded body produced by the production method of a calcium-based metallic glass alloy molded body for medical use of the present invention is characterized in that in an SBF (simulated body fluid) immersion test, a degradation rate in immersion for 5 h is 30 mass % or less.

The degradation rate of the calcium-based metallic glass alloy molded body in the simulated body fluid is measured by the SBF (simulated body fluid) immersion test or the like.

In the SBF immersion test for measuring the degradation rate in immersion for 0 h to 6 h, a calcium-based metallic glass alloy molded body molded in a mold having a diameter of 15 mm is cut and immersed in an SBF by hanging on a string, and the decrease in mass of the calcium-based metallic glass alloy molded body is measured on an hourly basis to determine the degradation rate. In the SBF immersion test, the mass counted as the mass of the calcium-based metallic glass alloy molded body is only that of the solid suspended from the string when the string is pulled up. For example, when the sample collapses and falls into the SBF, the mass thereof is not counted.

Examples

Hereinafter, the present invention will be specifically described with reference to examples and comparative examples, but the present invention is not limited to these examples at all.

Examples 1 to 12 and Comparative Examples 1 to 11 which have been made are summarized in Table 1.

TABLE 1

| | Metal composition | Alloying method and conditions | Sintering method and conditions |
|---|---|---|---|
| Example 1 | $Ca_{45}Mg_{25}Zn_{30}$ | Mechanical alloying method | (No sintering) * |
| Example 2 | $Ca_{45}Mg_{25}Zn_{30}$ | Casting method + mechanical alloying method (solid phase reaction 15 h) | (No sintering) * |
| Example 3 | $Ca_{65}Mg_{15}Zn_{20}$ | Gas atomization method | Spark plasma sintering method, sintering temperature 120° C. |
| Example 4 | $Ca_{65}Mg_{15}Zn_{20}$ | Gas atomization method | Spark plasma sintering method, sintering temperature 130° C. |
| Example 5 | $Ca_{65}Mg_{15}Zn_{20}$ | Gas atomization method | Spark plasma sintering method, sintering temperature 140° C. |
| Example 6 | $Ca_{65}Mg_{15}Zn_{20}$ + Fe (5 volume %) | Gas atomization method | Spark plasma sintering method, sintering temperature 140° C. |
| Example 7 | $Ca_{65}Mg_{15}Zn_{20}$ + Fe (10 volume %) | Gas atomization method | Spark plasma sintering method, sintering temperature 140° C. |
| Example 8 | $Ca_{65}Mg_{15}Zn_{20}$ + Fe (15 volume %) | Gas atomization method | Spark plasma sintering method, sintering temperature 140° C. |
| Example 9 | $Ca_{65}Mg_{15}Zn_{20}$ + Fe (20 volume %) | Gas atomization method | Spark plasma sintering method, sintering temperature 140° C. |
| Example 10 | $Ca_{65}Mg_{15}Zn_{20}$ | Gas atomization method | Spark plasma sintering method, sintering temperature 95° C. |
| Example 11 | $Ca_{55}Mg_{30}Zn_{15}$ | Casting method + mechanical alloying method (solid phase reaction 30 h) | (No sintering) * |
| Example 12 | $Ca_{55}Mg_{10}Zn_{35}$ | Casting method + mechanical alloying method (solid phase reaction 15 h) | (No sintering) * |
| Comparative Example 1 | $Ca_{45}Mg_{25}Zn_{30}$ | (No alloying) | — |
| Comparative Example 2 | $Ca_{65}Mg_{15}Zn_{20}$ | Casting method | — |
| Comparative Example 3 | $Ca_{65}Mg_{15}Zn_{20}$ | Gas atomization method | (No sintering) |
| Comparative Example 4 | $Ca_{65}Mg_{15}Zn_{20}$ | Gas atomization method | Spark plasma sintering method, sintering temperature 150° C. |
| Comparative Example 5 | $Ca_{65}Mg_{15}Zn_{20}$ | Gas atomization method | Spark plasma sintering method, sintering temperature 160° C. |
| Comparative Example 6 | $Ca_{65}Mg_{15}Zn_{20}$ + Fe (5 volume %) | Gas atomization method | (No sintering) |
| Comparative Example 7 | $Ca_{65}Mg_{15}Zn_{20}$ + Fe (10 volume %) | Gas atomization method | (No sintering) |
| Comparative Example 8 | $Ca_{65}Mg_{15}Zn_{20}$ + Fe (15 volume %) | Gas atomization method | (No sintering) |
| Comparative Example 9 | $Ca_{65}Mg_{15}Zn_{20}$ + Fe (20 volume %) | Gas atomization method | (No sintering) |
| Comparative Example 10 | Pure Ti | — | — |
| Comparative Example 11 | $Ca_{65}Mg_{15}Zn_{20}$ | Casting method | — |

* The specimen is used to confirm that the specimen is a metal glass before sintering.

(Confirmation of Metal Glass Generation by Mechanical Alloying Method)

The following test was carried out in order to confirm that the alloyed specimen is a metallic glass alloy powder having the properties of metal glass when the step of alloying the mixed metal powder of the present invention is a mechanical alloying method.

As indicated in Example 1 in Table 1, the $Ca_{45}Mg_{25}Zn_{30}$ mixed metal powder was subjected to alloying treatment by using a mechanical alloying device (Planetary Ball PM 100 type, manufactured by Retsch GmbH). The rotation speed of the chamber was 250 rpm, and the solid phase reaction time was 15 h.

A $Ca_{45}Mg_{25}Zn_{30}$ mixed metal powder which was not subjected to alloying as described in Comparative Example 1 was used for comparison.

Figure 5:
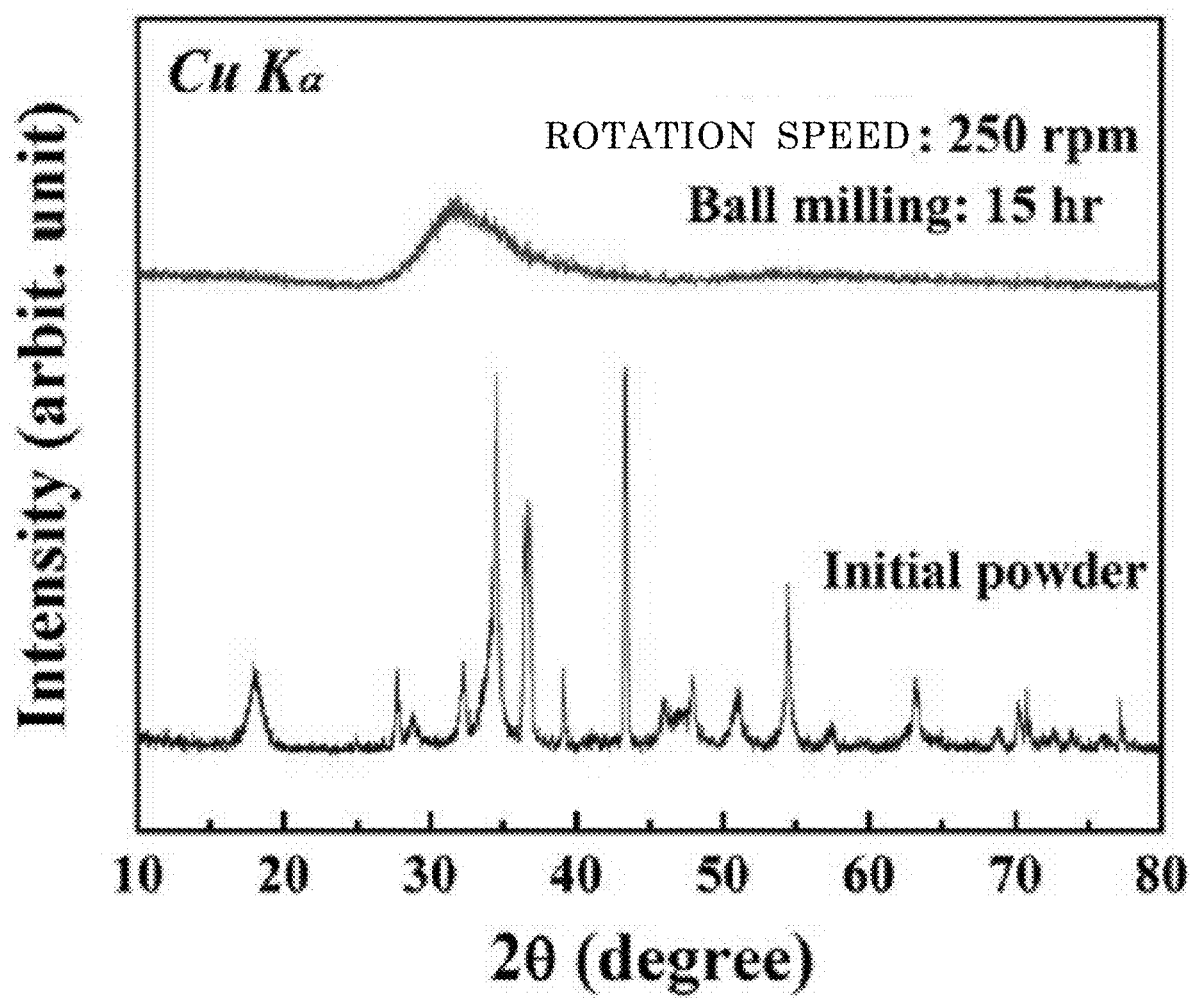
FIG. 5 depicts an X-ray diffraction spectrum (X-ray diffraction pattern) of a $Ca_{45}Mg_{25}Zn_{30}$ mixed metal powder and a $Ca_{45}Mg_{25}Zn_{30}$ metallic glass alloy made by a mechanical alloying method.

FIG. 5 depicts the X-ray diffraction pattern of the $Ca_{45}Mg_{25}Zn_{30}$ mixed metal powder (Comparative Example 1) and the $Ca_{45}Mg_{25}Zn_{30}$ metallic glass alloy powder made by the mechanical alloying method (Example 1). Ultima III manufactured by Rigaku Corporation was used as the X-ray diffraction device. It was confirmed that the $Ca_{45}Mg_{25}Zn_{30}$ mixed metal powder subjected to alloying treatment by the mechanical alloying method was a metallic glass alloy powder having the properties of metal glass.

Figure 6:
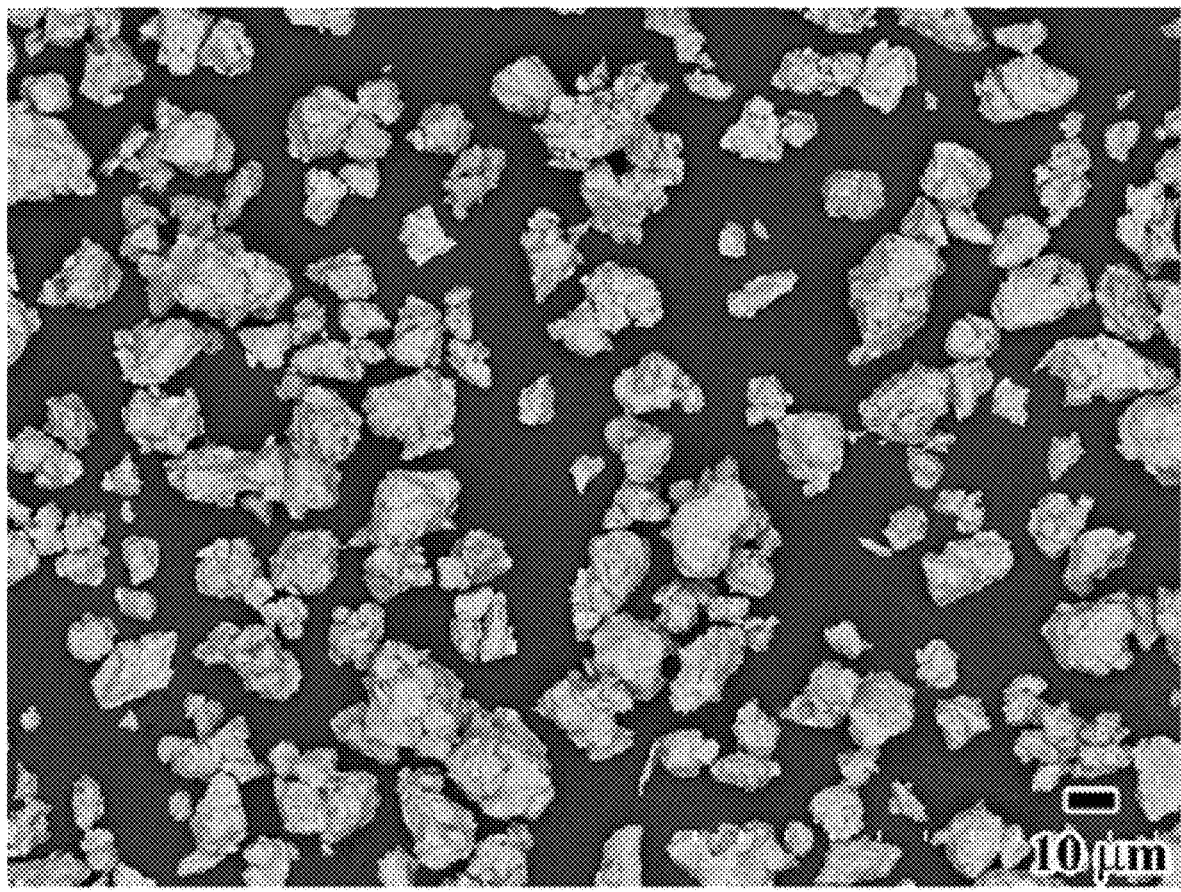
FIG. 6 depicts a scanning electron microscope (SEM) image of a $Ca_{45}Mg_{25}Zn_{30}$ metallic glass alloy powder made by a mechanical alloying method.

In addition, FIG. 6 depicts a scanning electron microscope image of the $Ca_{45}Mg_{25}Zn_{30}$ metallic glass alloy powder (Example 1) made by the mechanical alloying method described in Example 1. From FIG. 6, it was confirmed that the metallic glass alloy powder had a homogeneous shape.

(Confirmation of Metal Glass Generation by Method Using Mechanical Alloying Method in Combination with Casting Method)

The following test was carried out to confirm that the alloyed specimen is a metallic glass alloy powder having the properties of metal glass when the step of alloying the mixed metal powder of the present invention is a method of using the mechanical alloying method in combination with the casting method.

As described in Example 2 of Table 1, the $Ca_{45}Mg_{25}Zn_{30}$ mixed metal powder was first alloyed by a copper mold casting method. In the copper mold casting method, a BN crucible was used in a high-frequency melting furnace and a high-frequency induction heating device, melting was performed at 20 A under vacuum and Ar gas atmosphere, the $Ca_{45}Mg_{25}Zn_{30}$ mixed metal powder was high-frequency melted by heating for 5 min at 30 A, and the melt was cast into a copper mold having a diameter of 15 mm to make an ingot having a diameter of 15 mm and a length of 30 mm to 40 mm.

Next, the made ingot was cut and ball-milled by the mechanical alloying method to make a $Ca_{45}Mg_{25}Zn_{30}$ metallic glass alloy powder. The mass ratio of the stainless steel balls for ball milling and the ingot was 10:1, the rotation speed of the chamber was 250 rpm, and the solid phase reaction time was 15 h.

Further, the $Ca_{55}Mg_{10}Zn_{35}$ mixed metal powder represented as Example 11 in Table 1 was cast in the same manner as in Example 2 to make an ingot, and a $Ca_{55}Mg_{10}Zn_{35}$ metallic glass alloy powder was made by the mechanical alloying method. However, the solid phase reaction time in the mechanical alloying method was 30 h.

Furthermore, the $Ca_{55}Mg_{30}Zn_{15}$ mixed metal powder described in Example 12 in Table 1 was cast in the same manner as in Example 2 to make an ingot, and a $Ca_{55}M_{30}Zn_{15}$ metallic glass alloy powder was made by the mechanical alloying method. The solid phase reaction time in the mechanical alloying method was 15 h as in Example 2.

Figure 7A:
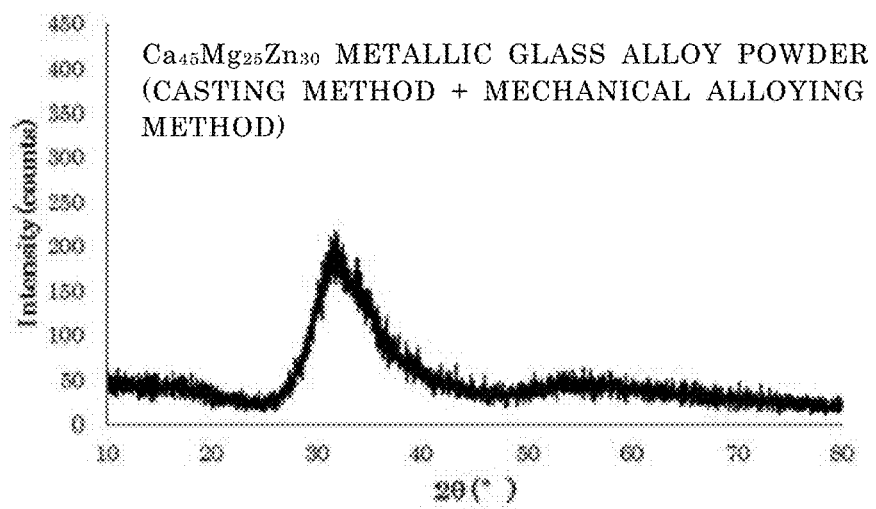
FIG. 7A depicts an X-ray diffraction spectrum (X-ray diffraction pattern) of a $Ca_{45}Mg_{25}Zn_{30}$ metallic glass alloy powder made by a mechanical alloying method after making an ingot by a casting method.

FIG. 7A depicts the X-ray diffraction pattern of the $Ca_{45}Mg_{25}Zn_{30}$ metallic glass alloy powder (Example 2) made by the mechanical alloying method after the ingot was made by the casting method. It was confirmed that the $Ca_{45}Mg_{25}Zn_{30}$ mixed metal powder subjected to the alloying treatment by the method using the mechanical alloying method in combination with the casting method was a metallic glass alloy powder having the properties of metal glass.

Figure 7B:
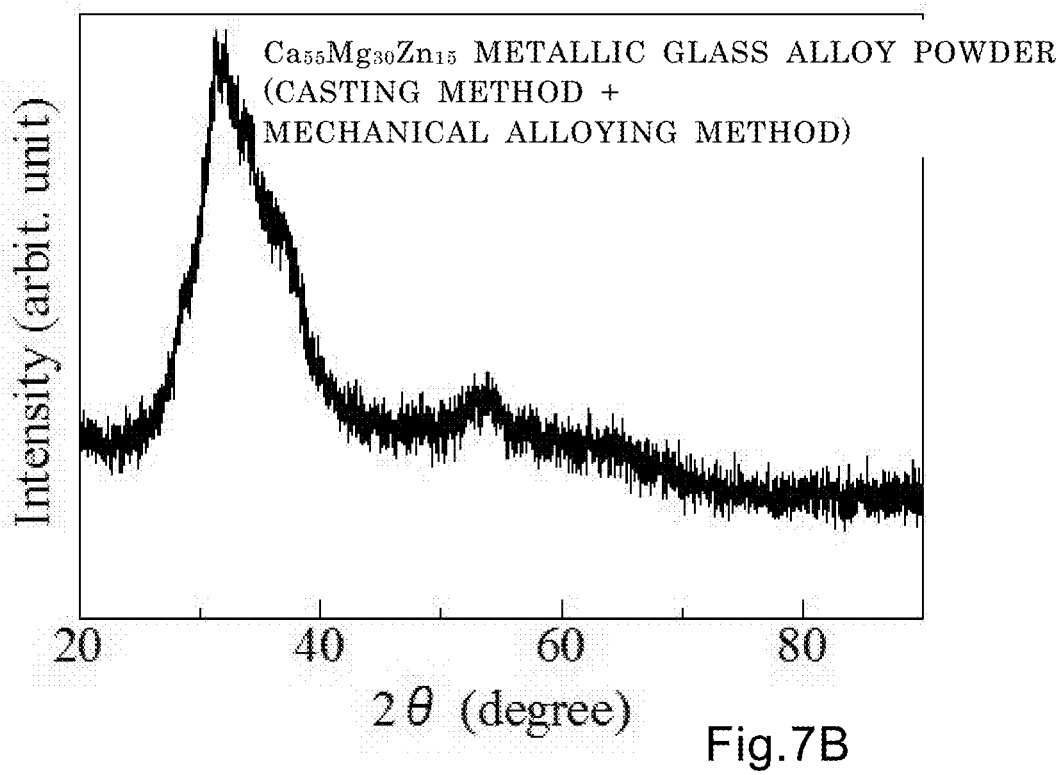
FIG. 7B depicts an X-ray diffraction spectrum (X-ray diffraction pattern) of a $Ca_{55}Mg_{30}Zn_{15}$ metallic glass alloy powder made by a mechanical alloying method after making an ingot by a casting method.

FIG. 7B depicts the X-ray diffraction pattern of the $Ca_{55}Mg_{30}Zn_{15}$ metallic glass alloy powder (Example 11) made by the mechanical alloying method after the ingot was made by the casting method. It was confirmed that the $Ca_{55}Mg_{30}Zn_{15}$ mixed metal powder subjected to the alloying treatment by the method using the mechanical alloying method in combination with the casting method was a metallic glass alloy powder having the properties of metal glass.

Figure 7C:
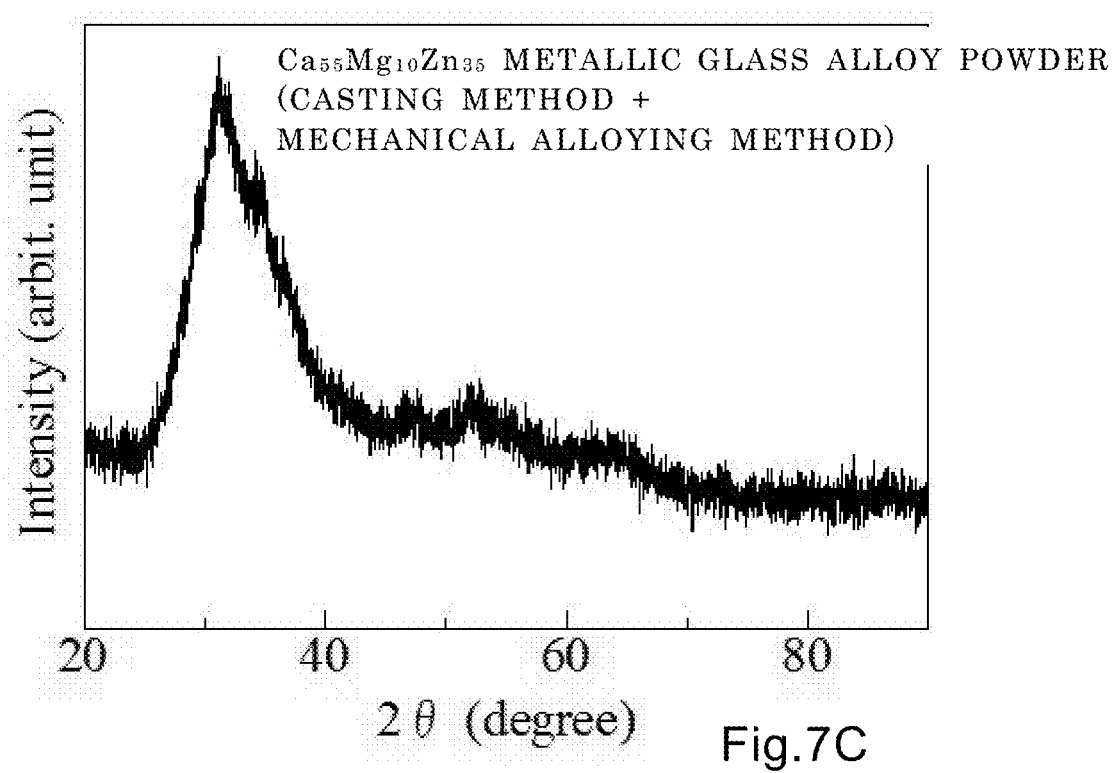
FIG. 7C depicts an X-ray diffraction spectrum (X-ray diffraction pattern) of a $Ca_{55}Mg_{10}Zn_{35}$ metallic glass alloy powder made by a mechanical alloying method after making an ingot by a casting method.

FIG. 7C depicts the X-ray diffraction pattern of the $Ca_{55}Mg_{10}Zn_{35}$ metallic glass alloy powder (Example 12) made by the mechanical alloying method after the ingot was made by the casting method. It was confirmed that the $Ca_{55}Mg_{10}Zn_{35}$ mixed metal powder subjected to the alloying treatment by the method using the mechanical alloying method in combination with the casting method was a metallic glass alloy powder having the properties of metal glass.

From Examples 2, 11 and 12, it was found that calcium-based mixed metal powders having different metal compositions were also metallic glass alloy powders having the properties of metal glass.

(Confirmation of Presence or Absence of Generation of Metal Glass in Casting Method)

The following test was carried out in order to confirm whether or not the alloyed specimen is a metallic glass alloy powder having the properties of metal glass when alloying the mixed metal powder of the present invention is a casting method.

As indicated in Comparative Example 2 of Table 1, the $Ca_{65}Mg_{15}Zn_{20}$ mixed metal powder was alloyed by a copper mold casting method. In the copper mold casting method, a BN crucible was used in a high-frequency melting furnace and a high-frequency induction heating device, melting was performed at 20 A under vacuum and Ar gas atmosphere, the $Ca_{65}Mg_{15}Zn_{20}$ mixed metal powder was high-frequency melted by heating for 5 min at 30 A, and the melt was cast into a copper mold having a diameter of 15 mm to make an ingot having a diameter of 15 mm and a length of 30 mm to 40 mm.

Figure 8:
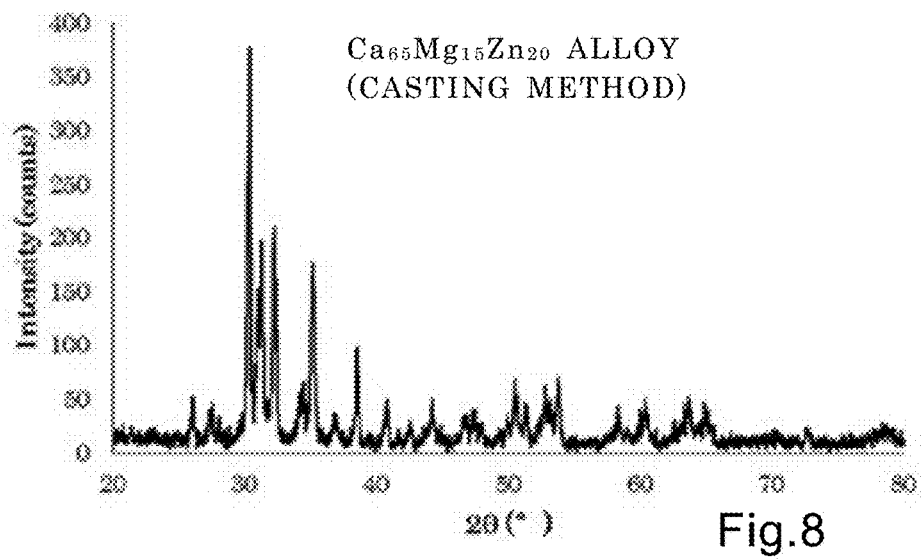
FIG. 8 depicts an X-ray diffraction spectrum (X-ray diffraction pattern) of a $Ca_{65}Mg_{15}Zn_{20}$ alloy made by a casting method.
Figure 9A:
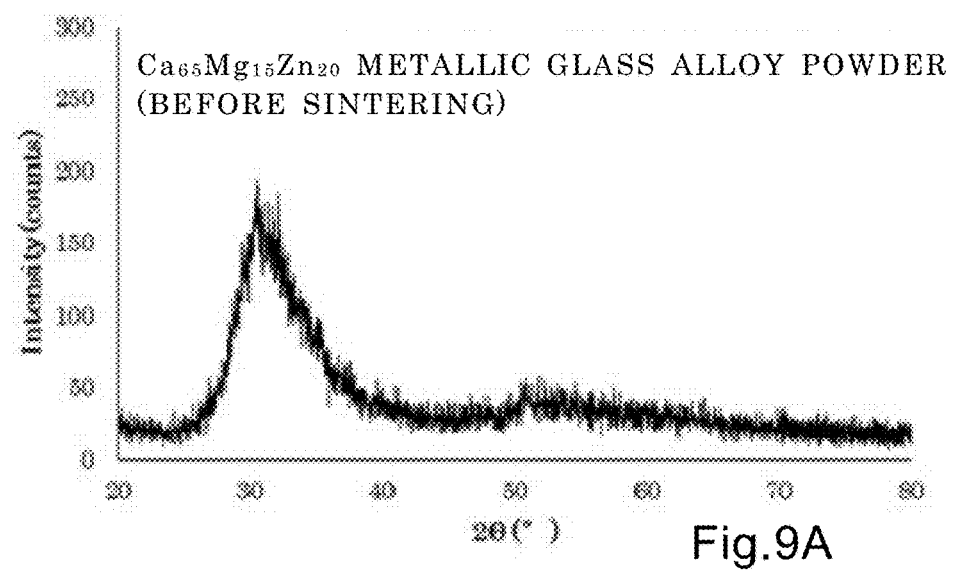
FIG. 9A depicts an X-ray diffraction spectrum (X-ray diffraction pattern) of a $Ca_{65}Mg_{15}Zn_{20}$ metallic glass alloy powder made by a gas atomization method.
Figure 9B:
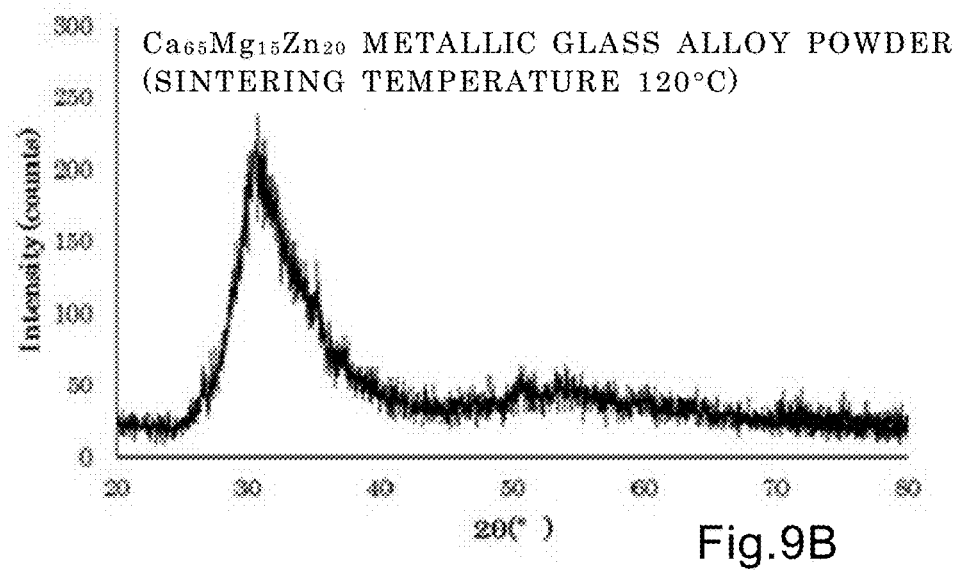
FIG. 9B depicts an X-ray diffraction spectrum (X-ray diffraction pattern) of a $Ca_{65}Mg_{15}Zn_{20}$ metallic glass alloy molded body made at a sintering temperature of 120° C. by a spark plasma sintering method after making a $Ca_{65}Mg_{15}Zn_{20}$ metallic glass alloy powder by a gas atomization method.
Figure 9C:
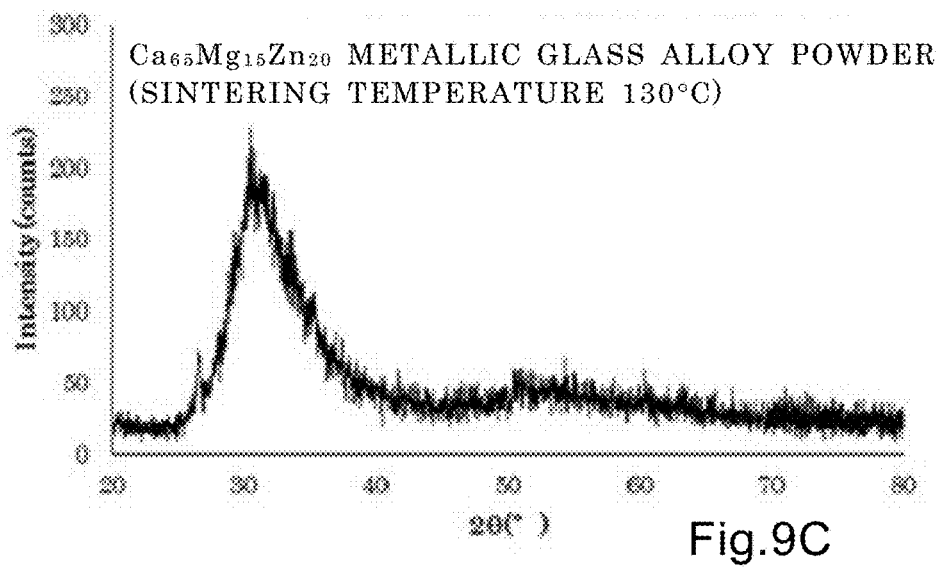
FIG. 9C depicts an X-ray diffraction spectrum (X-ray diffraction pattern) of a $Ca_{65}Mg_{15}Zn_{20}$ metallic glass alloy molded body made at a sintering temperature of 130° C. by a spark plasma sintering method after making a $Ca_{65}Mg_{15}Zn_{20}$ metallic glass alloy powder by a gas atomization method.
Figure 9D:
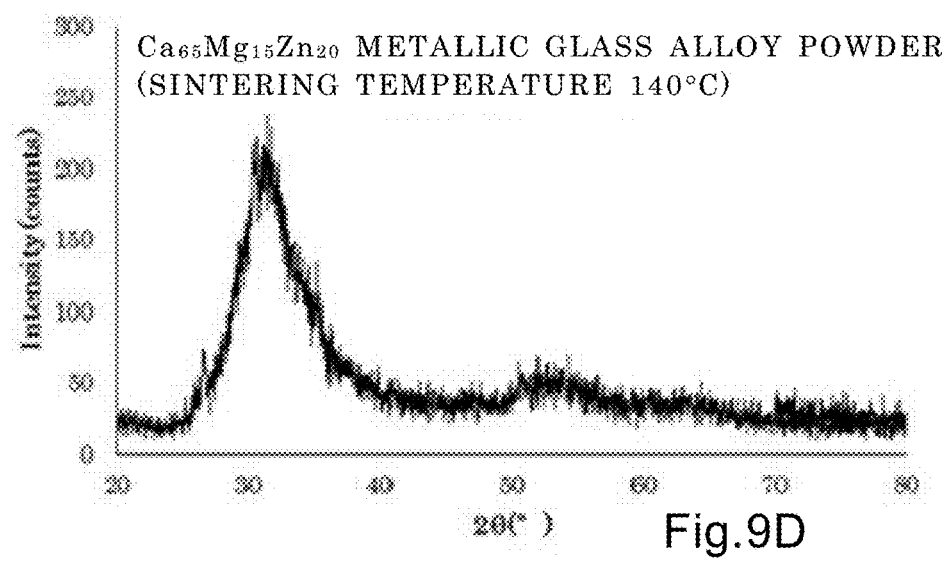
FIG. 9D depicts an X-ray diffraction spectrum (X-ray diffraction pattern) of a $Ca_{65}Mg_{15}Zn_{20}$ metallic glass alloy molded body made at a sintering temperature of 140° C. by a spark plasma sintering method after making a $Ca_{65}Mg_{15}Zn_{20}$ metallic glass alloy powder by a gas atomization method.
Figure 9E:
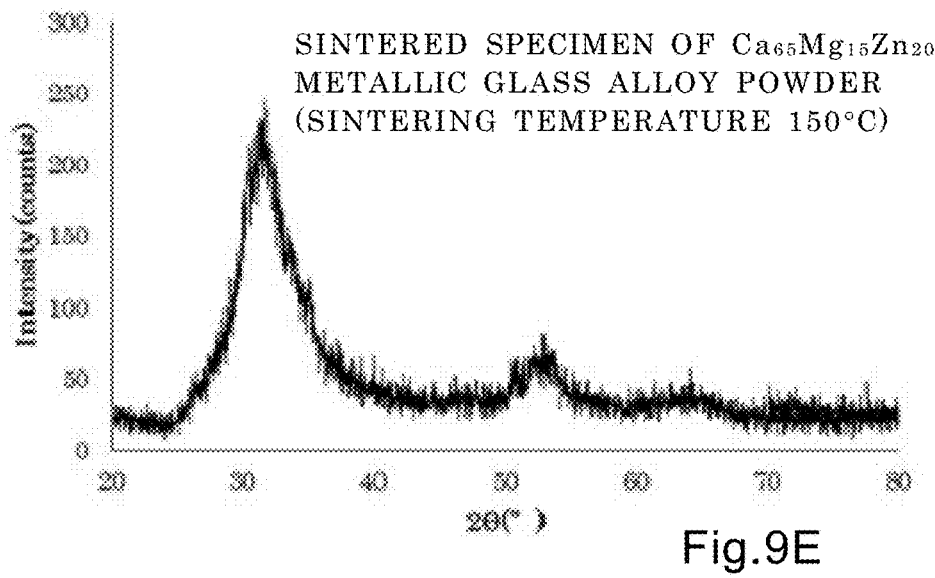
FIG. 9E depicts an X-ray diffraction spectrum (X-ray diffraction pattern) of a sintered specimen of a $Ca_{65}Mg_{15}Zn_{20}$ metallic glass alloy powder made at a sintering temperature of 150° C. by a spark plasma sintering method after making a $Ca_{65}Mg_{15}Zn_{20}$ metallic glass alloy powder by a gas atomization method.
Figure 9F:
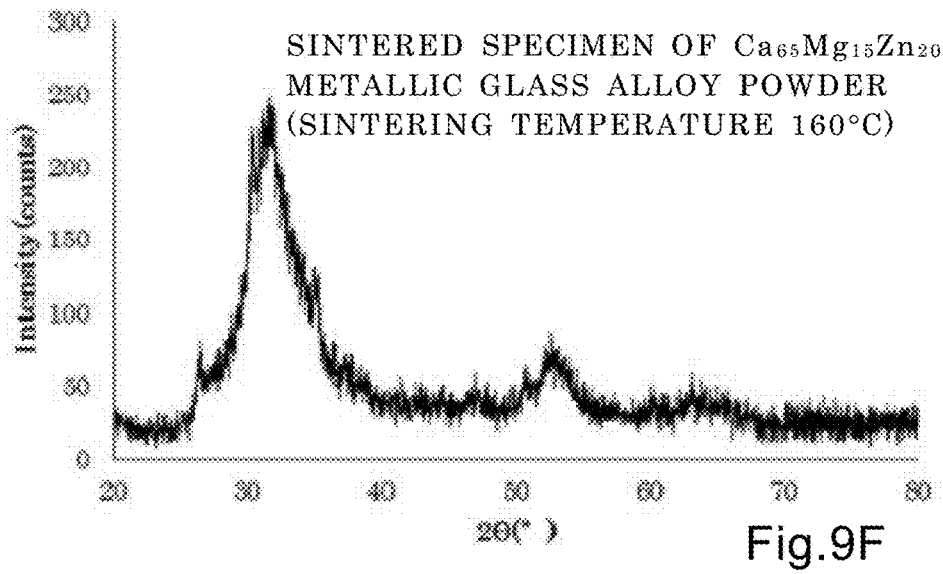
FIG. 9F depicts an X-ray diffraction spectrum (X-ray diffraction pattern) of a sintered specimen of a $Ca_{65}Mg_{15}Zn_{20}$ metallic glass alloy powder made at a sintering temperature of 160° C. by a spark plasma sintering method after making a $Ca_{65}Mg_{15}Zn_{20}$ metallic glass alloy powder by a gas atomization method.
Figure 10A:
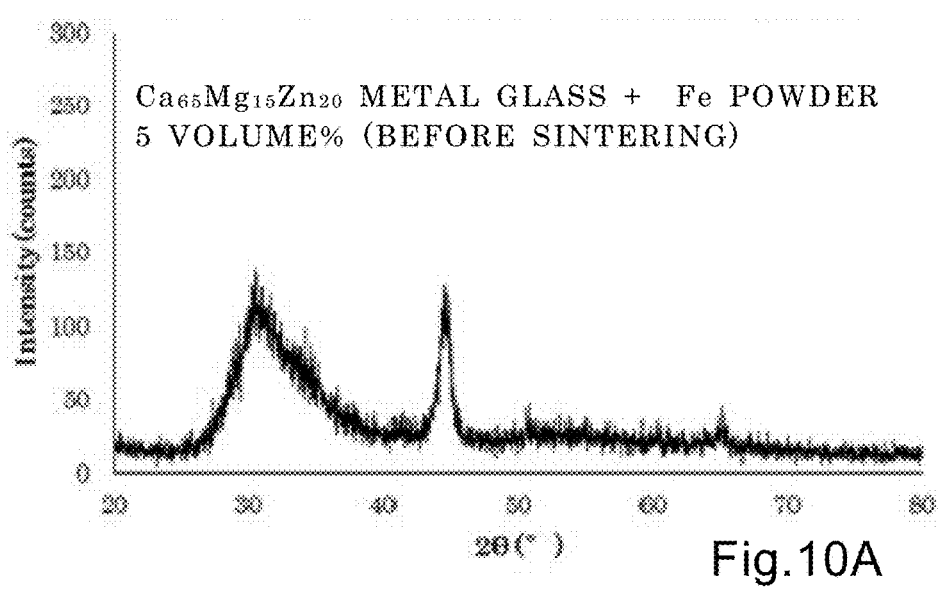
FIG. 10A depicts an X-ray diffraction spectrum (X-ray diffraction pattern) of a specimen in which Fe crystal grains are dispersed at 5 volume % after making a $Ca_{65}Mg_{15}Zn_{20}$ metallic glass alloy powder by a gas atomization method.
Figure 10B:
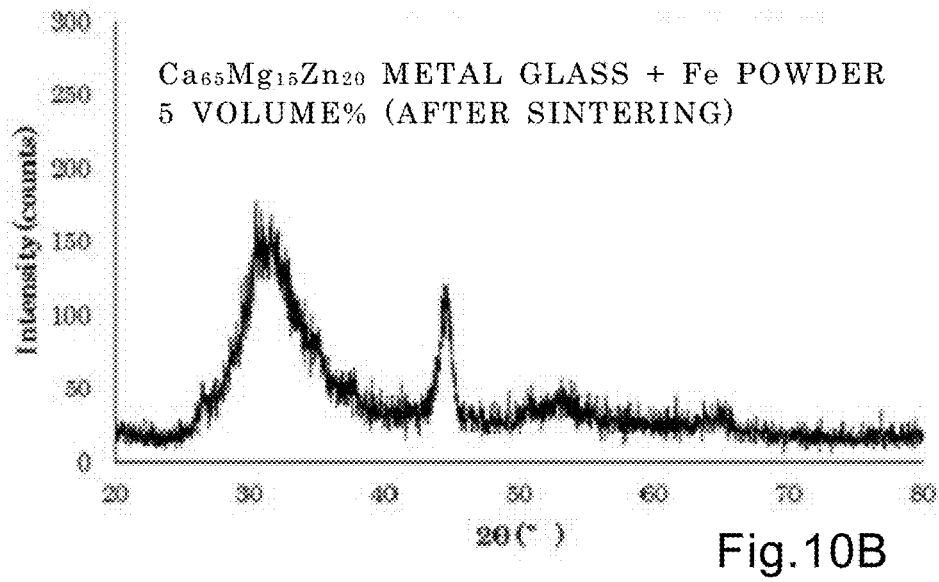
FIG. 10B depicts an X-ray diffraction spectrum (X-ray diffraction pattern) of a metallic glass alloy molded body made by a spark plasma sintering method in which Fe crystal grains are dispersed at 5 volume % after making $Ca_{65}Mg_{15}Zn_{20}$ metallic glass alloy powder by a gas atomization method.
Figure 10C:
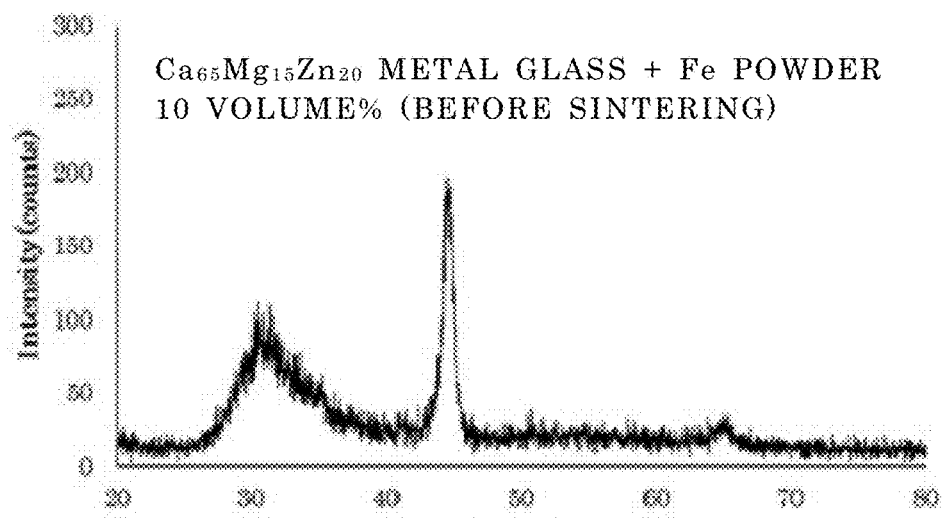
FIG. 10C depicts an X-ray diffraction spectrum (X-ray diffraction pattern) of a specimen in which Fe crystal grains are dispersed at 10 volume % after making a $Ca_{65}Mg_{15}Zn_{20}$ metallic glass alloy powder by a gas atomization method.
Figure 10D:
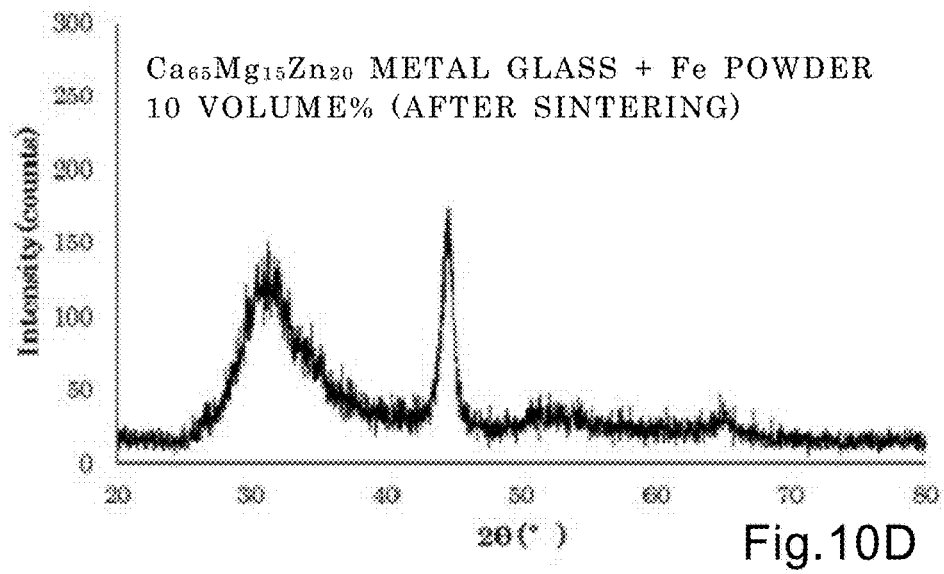
FIG. 10D depicts an X-ray diffraction spectrum (X-ray diffraction pattern) of a metallic glass alloy molded body made by a spark plasma sintering method in which Fe crystal grains are dispersed at 10 volume % after making $Ca_{65}Mg_{15}Zn_{20}$ metallic glass alloy powder by a gas atomization method.
Figure 10E:
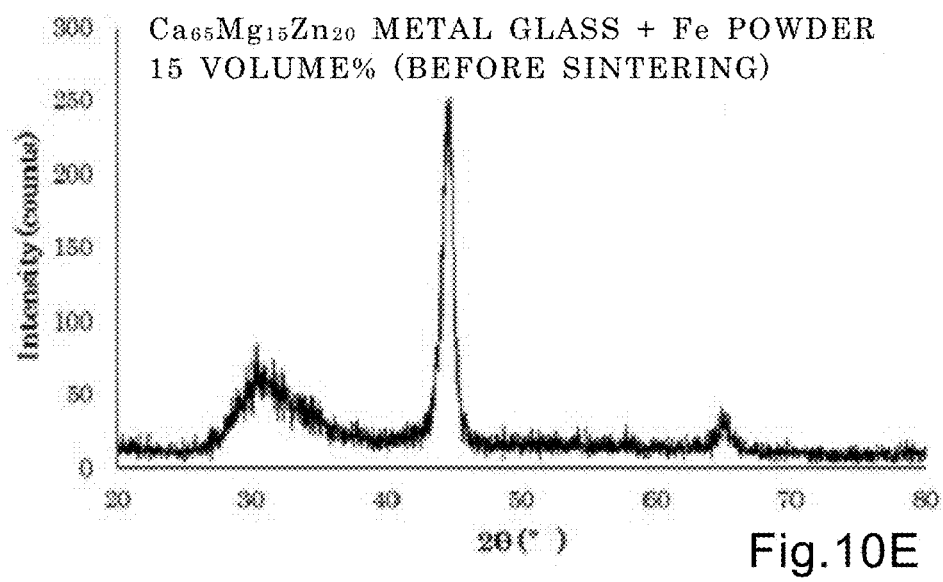
FIG. 10E depicts an X-ray diffraction spectrum (X-ray diffraction pattern) of a specimen in which Fe crystal grains are dispersed at 15 volume % after making a $Ca_{65}Mg_{15}Zn_{20}$ metallic glass alloy powder by a gas atomization method.
Figure 10F:
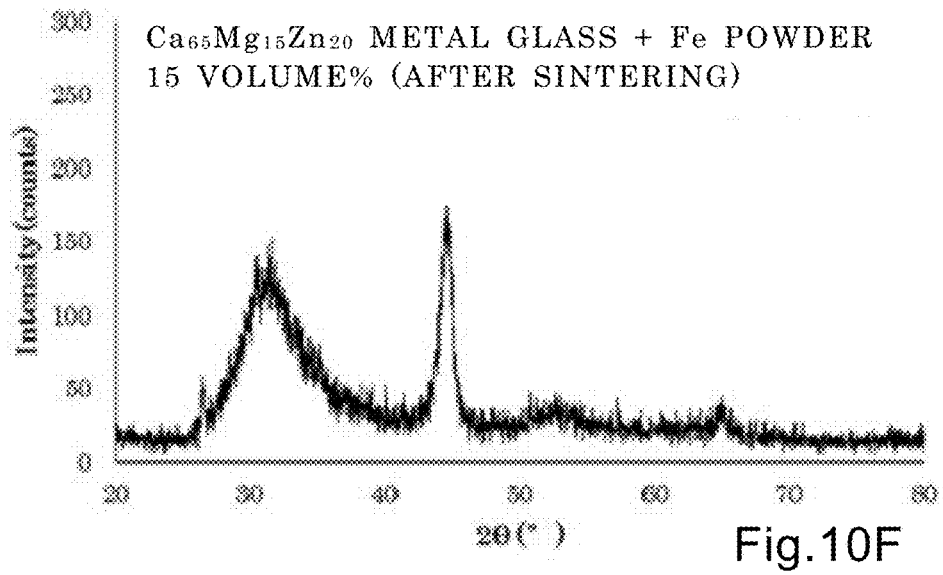
FIG. 10F depicts an X-ray diffraction spectrum (X-ray diffraction pattern) of a metallic glass alloy molded body made by a spark plasma sintering method in which Fe crystal grains are dispersed at 15 volume % after making $Ca_{65}Mg_{15}Zn_{20}$ metallic glass alloy powder by a gas atomization method.
Figure 10G:
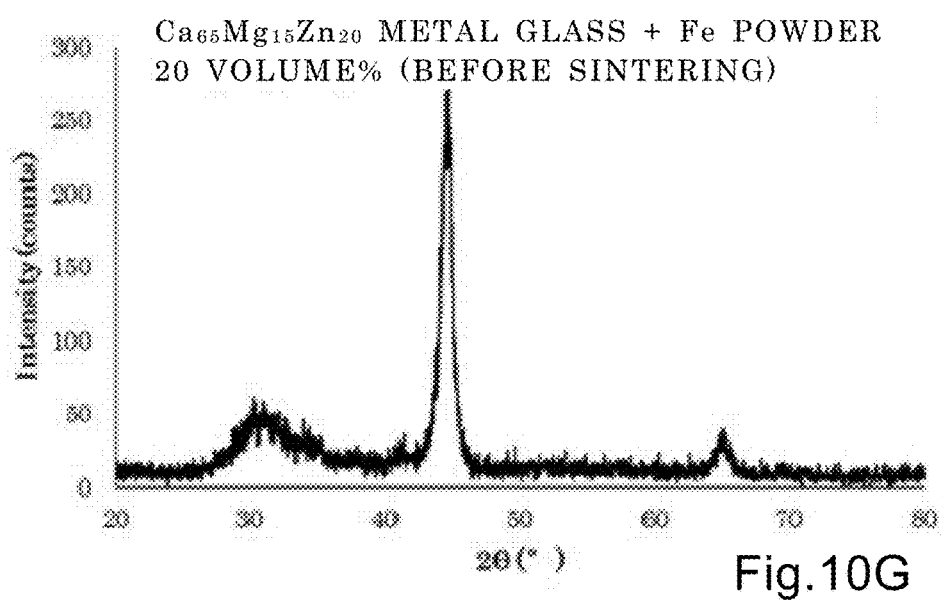
FIG. 10G depicts an X-ray diffraction spectrum (X-ray diffraction pattern) of a specimen in which Fe crystal grains are dispersed at 20 volume % after making a $Ca_{65}Mg_{15}Zn_{20}$ metallic glass alloy powder by a gas atomization method.
Figure 10H:
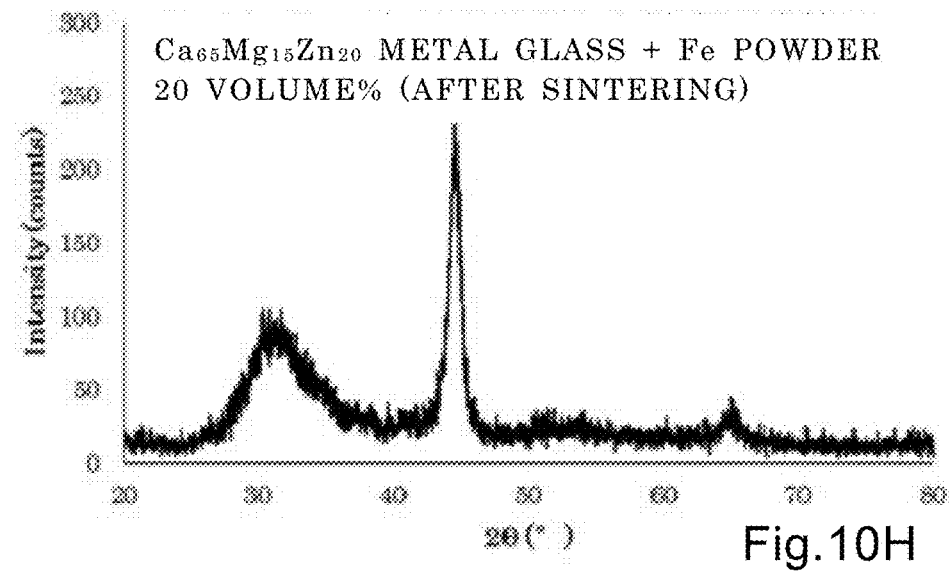
FIG. 10H depicts an X-ray diffraction spectrum (X-ray diffraction pattern) of a metallic glass alloy molded body made by a spark plasma sintering method in which Fe crystal grains are dispersed at 20 volume % after making $Ca_{65}Mg_{15}Zn_{20}$ metallic glass alloy powder by a gas atomization method.
Figure 11A:
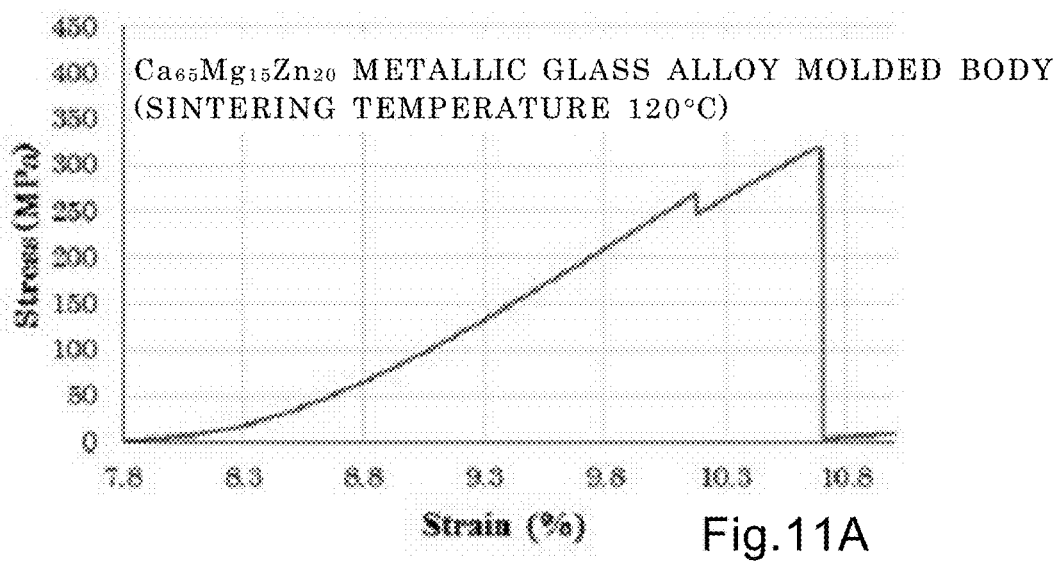
FIG. 11A depicts compression test results of a $Ca_{65}Mg_{15}Zn_{20}$ metallic glass alloy molded body made at a sintering temperature of 120° C. by a spark plasma sintering method after making a $Ca_{65}Mg_{15}Zn_{20}$ metallic glass alloy powder by a gas atomization method.
Figure 11B:
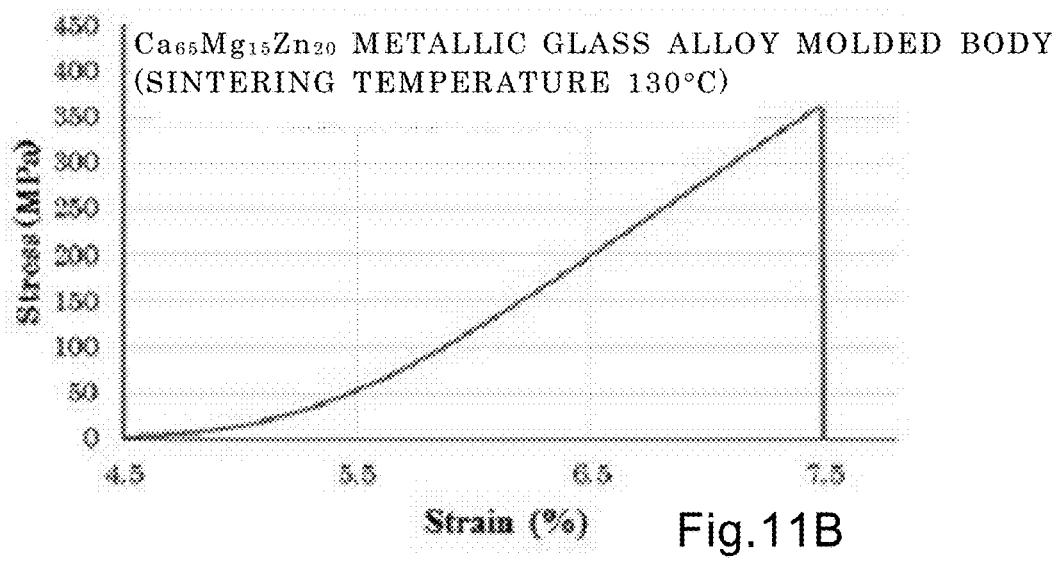
FIG. 11B depicts compression test results of a $Ca_{65}Mg_{15}Zn_{20}$ metallic glass alloy molded body made at a sintering temperature of 130° C. by a spark plasma sintering method after making a $Ca_{65}Mg_{15}Zn_{20}$ metallic glass alloy powder by a gas atomization method.
Figure 11C:
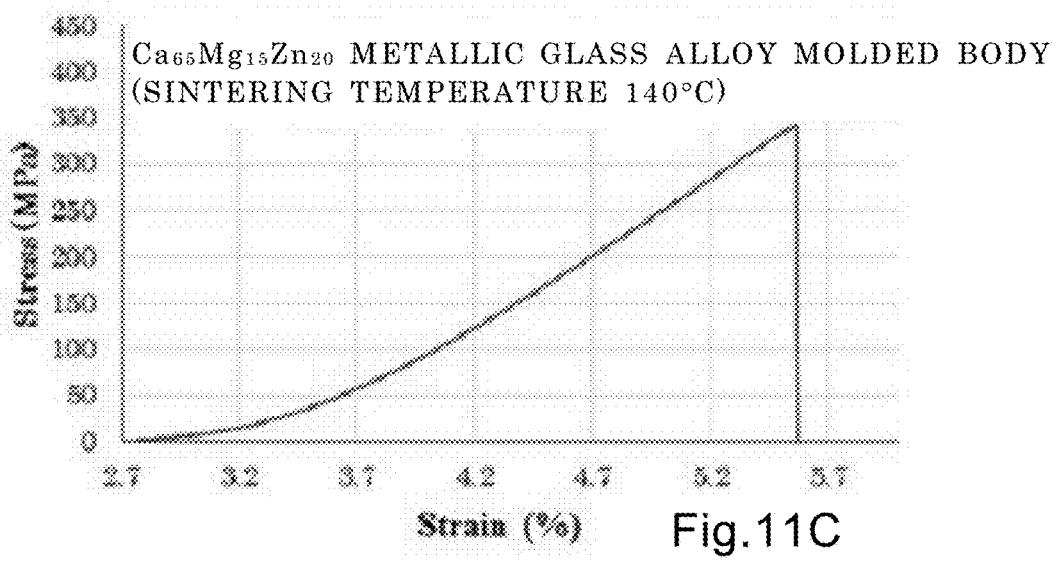
FIG. 11C depicts compression test results of a $Ca_{65}Mg_{15}Zn_{20}$ metallic glass alloy molded body made at a sintering temperature of 140° C. by a spark plasma sintering method after making a $Ca_{65}Mg_{15}Zn_{20}$ metallic glass alloy powder by a gas atomization method.
Figure 11D:
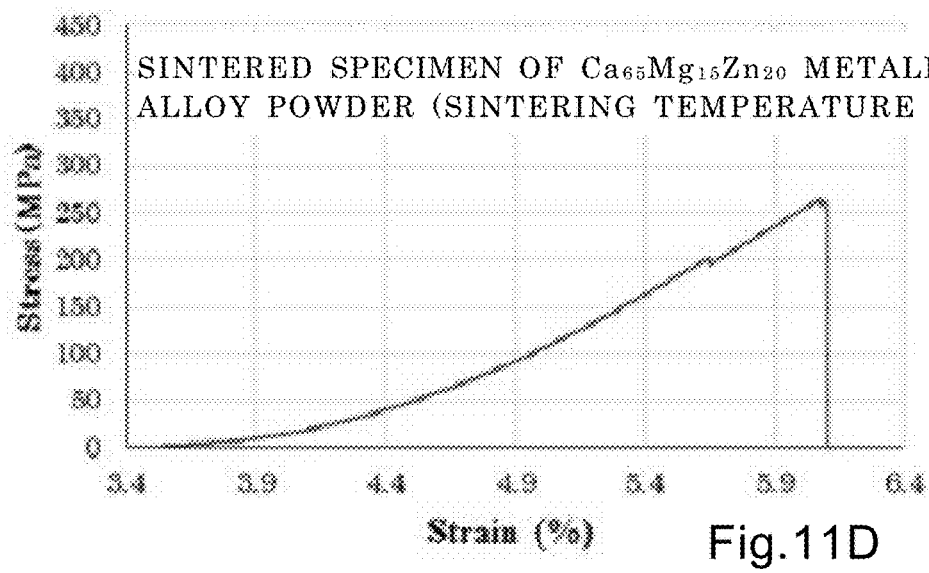
FIG. 11D depicts compression test results of a sintered specimen of a $Ca_{65}Mg_{15}Zn_{20}$ metallic glass alloy powder made at a sintering temperature of 150° C. by a spark plasma sintering method after making a $Ca_{65}Mg_{15}Zn_{20}$ metallic glass alloy powder by a gas atomization method.
Figure 11E:
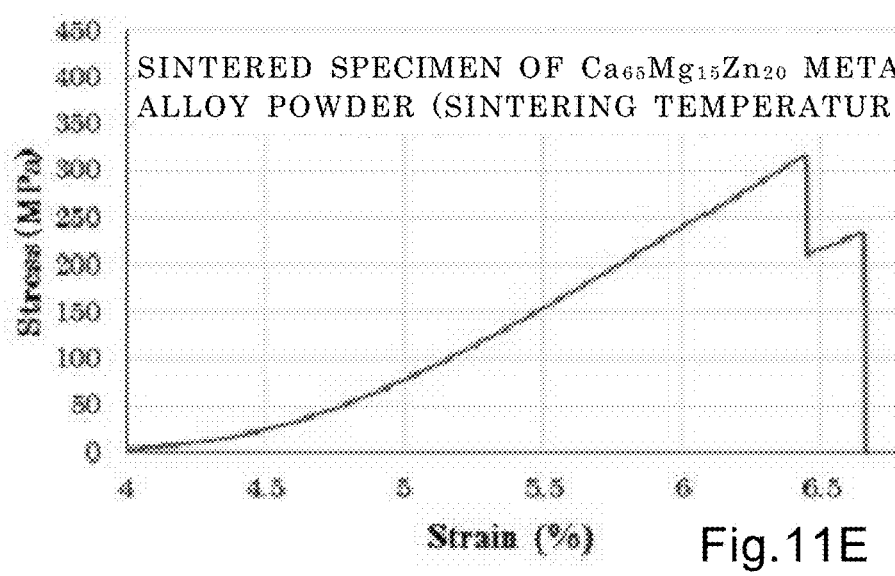
FIG. 11E depicts compression test results of a sintered specimen of a $Ca_{65}Mg_{15}Zn_{20}$ metallic glass alloy powder made at a sintering temperature of 160° C. by a spark plasma sintering method after making a $Ca_{65}Mg_{15}Zn_{20}$ metallic glass alloy powder by a gas atomization method.

FIG. 8 depicts the X-ray diffraction pattern of the $Ca_{65}Mg_{15}Zn_{20}$ alloy (ingot, Comparative Example 2) made by the casting method. It was confirmed that the $Ca_{65}Mg_{15}Zn_{20}$ mixed metal powder subjected to alloying treatment by the casting method did not have the properties of metal glass.

(Confirmation of Crystallization of Metal Glass by Sintering Temperature)

The following test was carried out in order to confirm whether or not the metallic glass alloy molded body is crystallized depending on the sintering temperature when the step of sintering the alloyed mixed metal powder (metallic glass alloy powder) of the present invention is the spark plasma sintering method.

As indicated in Examples 3 to 5 and Comparative Examples 4 and 5 in Table 1, a $Ca_{65}Mg_{15}Zn_{20}$ metallic glass alloy powder was made by a gas atomization method, and then a $Ca_{65}Mg_{15}Zn_{20}$ metallic glass alloy molded body was made by a spark plasma sintering method. The gas atomization method was set to the conditions of a temperature of about 650 K and an Ar gas injection pressure of about 8 MPa by using a gas atomizer (small gas atomization device, model number VF-RQP200, manufactured by MAKABE Technical Research Co., Ltd.). In the spark plasma sintering method, the $Ca_{65}Mg_{15}Zn_{20}$ metallic glass alloy powder of 53 μm or less was treated by using a spark plasma sintering device (SPS-3.20 MK-IV manufactured by SPS SYNTECS CORPORATION) under the conditions set to a loading pressure of 600 MPa, a holding time of 10 min after reaching the sintering temperature, and a sintering temperature of 120° C. to 160° C.

FIGS. 9A to 9F depict X-ray diffraction patterns of the $Ca_{65}Mg_{15}Zn_{20}$ metallic glass alloy powder (Comparative Example 3) before sintering and the $Ca_{65}Mg_{15}Zn_{20}$ metallic glass alloy molded body (Examples 3 to 5 and Comparative Examples 4 and 5) for each sintering temperature.

It was recognized that the molded body maintained the properties of metal glass up to a sintering temperature of 140° C., but when the sintering temperature reached 150° C. or higher, a peak indicating crystallization of the metal glass was confirmed. Therefore, it was found that the optimum sintering temperature in the production of the calcium-based metallic glass alloy molded body of the present invention was 140° C.

(Test of Making $Ca_{65}Mg_{15}Zn_{20}$ Metallic Glass Alloy Molded Body with Dispersed Fe Crystal Grains—1—)

The following test was carried out in order to confirm whether or not the properties of metal glass of the calcium-based metallic glass alloy molded body are affected when the step of dispersing Fe crystal grains is added between the step of alloying and the step of sintering the alloyed mixed metal powder according to the present invention.

As indicated in Examples 6 to 9 and Comparative Examples 6 to 9 in Table 1, a $Ca_{65}Mg_{15}Zn_{20}$ metallic glass alloy powder was made by a gas atomization method, and Fe crystal grains having a grain size of 3 μm to 5 μm were then dispersed in an amount of 5 volume % to 20 volume % to make specimens before sintering (Comparative Examples 6 to 9) and specimens sintered at a sintering temperature of 140° C. (Examples 6 to 9).

FIGS. 10A to 10H depict X-ray diffraction patterns before and after sintering of the $Ca_{65}Mg_{15}Zn_{20}$ metallic glass alloy powders with dispersed Fe crystal grains in which Fe crystal grains were dispersed in an amount of 5 volume % to 20 volume % (A: Comparative Example 6, B: Example 6, C: Comparative Example 7, D: Example 7, E: Comparative Example 8, F: Example 8, G: Comparative Example 9, and H: Example 9).

It was found that the properties of metal glass of the calcium-based metallic glass alloy molded body practically were not changed by sintering of the $Ca_{65}Mg_{15}Zn_{20}$ metallic glass alloy powders with dispersed Fe crystal grains for all volume fractions of dispersed Fe crystal grains.

(Effect of Sintering Temperature on Compressive Strength of Metallic Glass Alloy Molded Body)

The following test was carried out in order to measure the effect of sintering temperature on the compressive strength of the metallic glass alloy molded body when the step of sintering the alloyed mixed metal powder (metallic glass alloy powder) of the present invention is a spark plasma sintering method.

As indicated in Examples 3 to 5 and Comparative Examples 4 and 5 in Table 1, a $Ca_{65}Mg_{15}Zn_{20}$ metallic glass alloy powder was made by a gas atomization method, and a $Ca_{65}Mg_{15}Zn_{20}$ metallic glass alloy molded body was then made by a spark plasma sintering method at a sintering temperature of 120° C. to 160° C. In the spark plasma sintering method, the $Ca_{65}Mg_{15}Zn_{20}$ metallic glass alloy powder of 53 μm or less was treated under the conditions set to a loading pressure of 600 MPa, a holding time of 10 min after reaching the sintering temperature, and a sintering temperature of 120° C. to 160° C.

A specimen obtained by alloying the $Ca_{65}Mg_{15}Zn_{20}$ mixed metal powder indicated as Comparative Example 2 in Table 1 by a copper mold casting method was used as a comparative specimen.

For comparison, a pure titanium specimen indicated as Comparative Example 10 in Table 1 was used.

In the compression tests of the specimens of Examples 3 to 5 and Comparative Examples 2, 4, and 5, quadrangular prism-shaped measurement pieces having a width of 2 mm, a thickness of 2 mm, and a height of 4 mm were made, and the relationship between compressive strength and strain was measured at a constant crosshead speed corresponding to an initial strain rate of $5 \times 10^{-4}$ mm/s under uniaxial pressure by using a conventional mechanical test machine (high-temperature vacuum tensile/compression tester AG50VF, manufactured by Shimadzu Corporation).

The compression test of the specimen of Comparative Example 10 was similarly carried out by using a conventional mechanical test machine (high-temperature vacuum tensile/compression tester AG50VF, manufactured by Shimadzu Corporation) with respect to a specimen having a diameter of 1.48 mm and a height of 3.78 mm.

Figure 12:
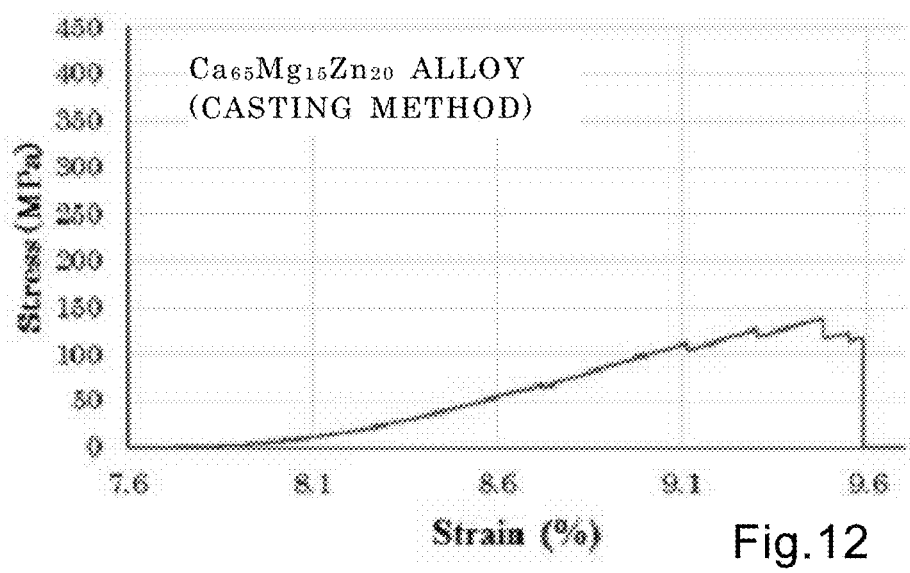
FIG. 12 depicts compression test results of a $Ca_{65}Mg_{15}Zn_{20}$ alloy made by a casting method.
Figure 13A:
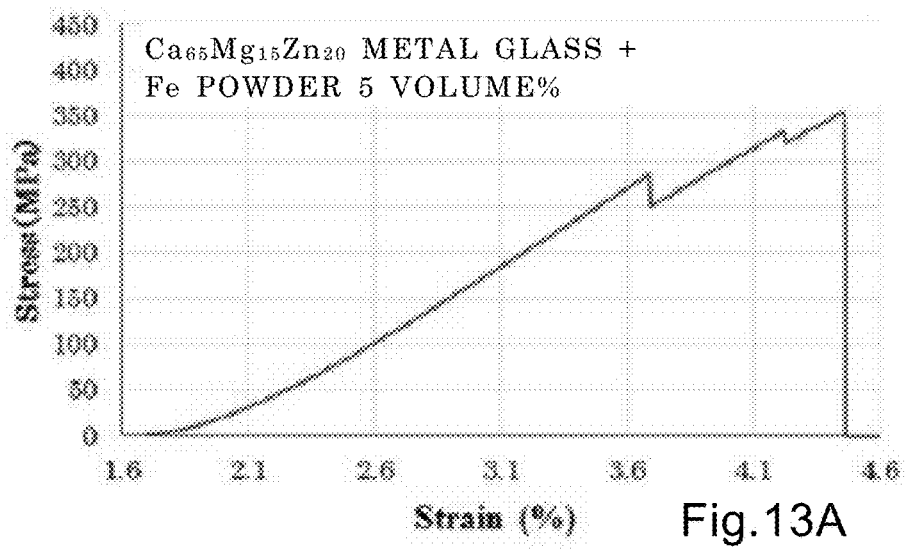
FIG. 13A depicts compression test results of a metallic glass alloy molded body made by a spark plasma sintering method in which 5 volume % of Fe crystal grains are dispersed after making a $Ca_{65}Mg_{15}Zn_{20}$ metallic glass alloy powder by a gas atomization method.
Figure 13B:
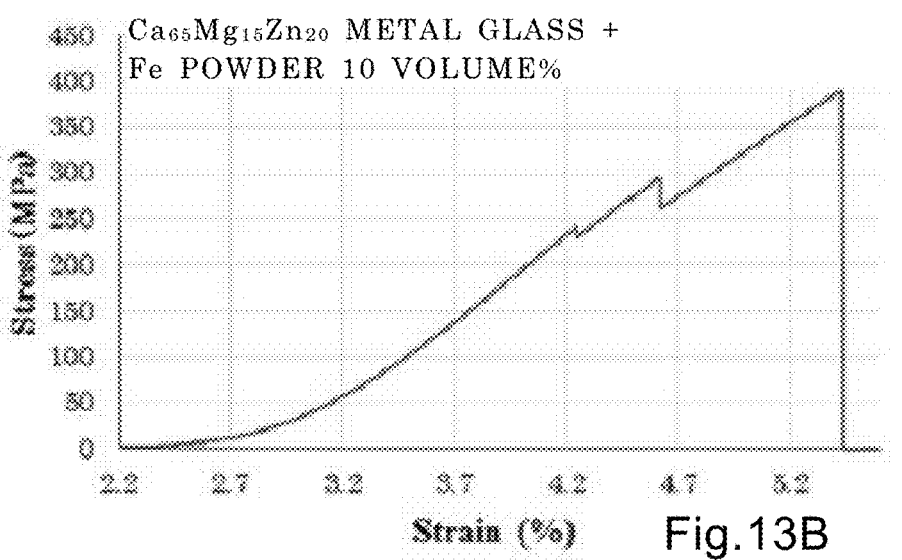
FIG. 13B depicts compression test results of a metallic glass alloy molded body made by a spark plasma sintering method in which 10 volume % of Fe crystal grains are dispersed after making a $Ca_{65}Mg_{15}Zn_{20}$ metallic glass alloy powder by a gas atomization method.
Figure 13C:
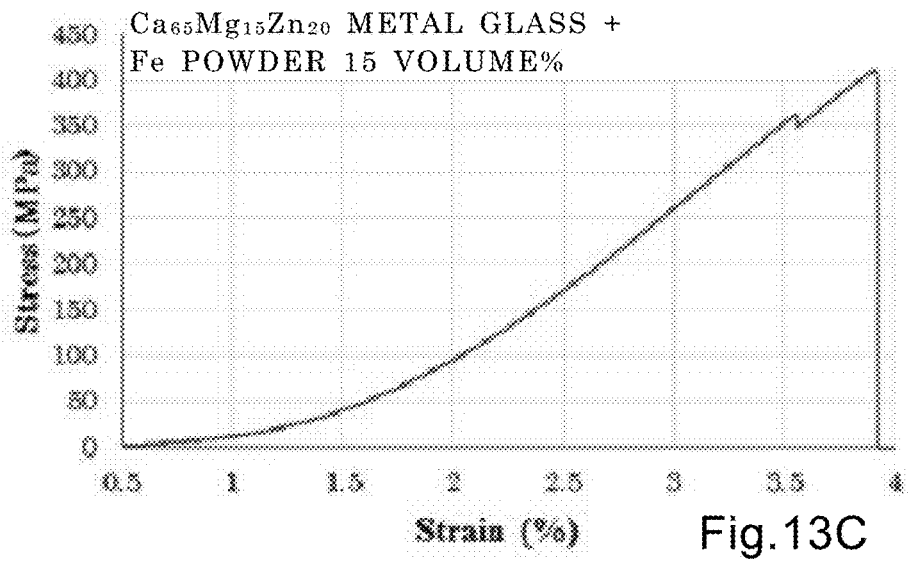
FIG. 13C depicts compression test results of a metallic glass alloy molded body made by a spark plasma sintering method in which 15 volume % of Fe crystal grains are dispersed after making a $Ca_{65}Mg_{15}Zn_{20}$ metallic glass alloy powder by a gas atomization method.
Figure 13D:
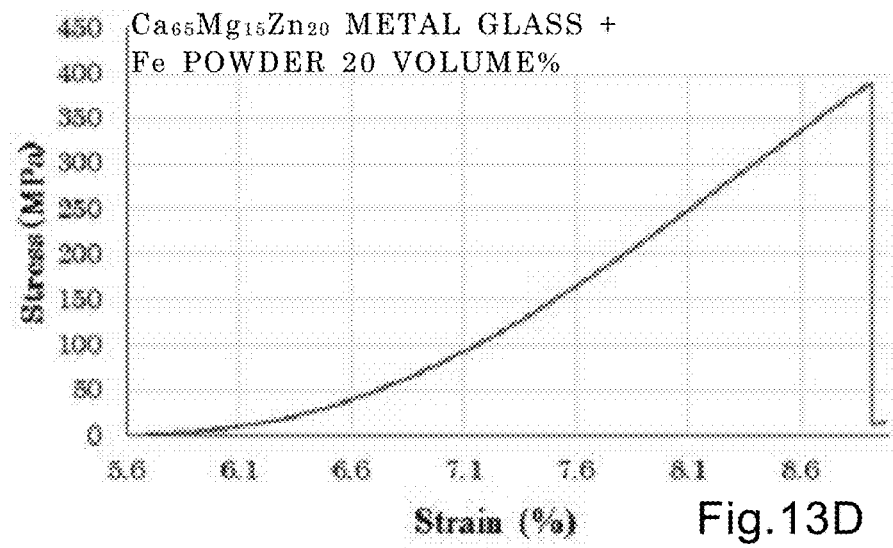
FIG. 13D depicts compression test results of a metallic glass alloy molded body made by a spark plasma sintering method in which 20 volume % of Fe crystal grains are dispersed after making a $Ca_{65}Mg_{15}Zn_{20}$ metallic glass alloy powder by a gas atomization method.
Figure 14:
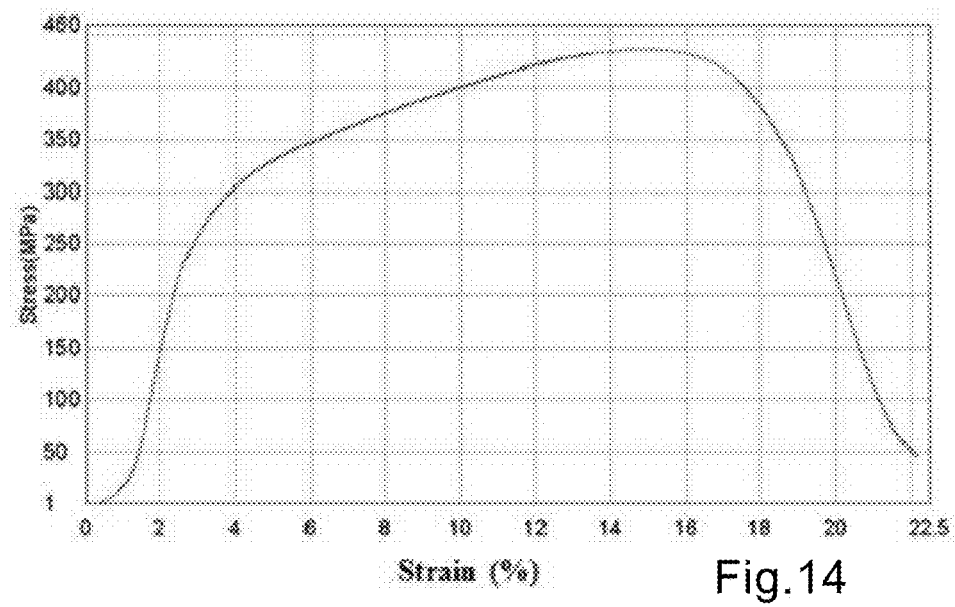
FIG. 14 depicts compression test results of a pure titanium specimen.

The compression test results are depicted in FIGS. 11A to 11E (Examples 3 to 5, Comparative Examples 4 and 5), FIG. 12 (Comparative Example 2), and FIG. 14 (Comparative Example 10).

The compressive strength of each specimen which is determined based on the compression test results is depicted in Table 2.

TABLE 2

|  | Sintering temperature (° C.) | Compressive strength (MPa) |
| --- | --- | --- |
| Example 3 | 120 | 320.20 |
| Example 4 | 130 | 361.59 |
| Example 5 | 140 | 342.01 |
| Comparative Example 4 | 150 | 262.54 |
| Comparative Example 5 | 160 | 317.75 |
| Comparative Example 2 | — | 117.92 |
| Comparative Example 10 | — | 436 |

As indicated by Examples 3 to 5 in Table 2, it was found that the sintered specimen of the $Ca_{65}Mg_{15}Zn_{20}$ metallic glass alloy powder produced by setting the sintering temperature in the spark plasma sintering method to 120° C. to 140° C. had a compressive strength of 320 MPa or more.

Meanwhile, as indicated by Comparative Example 4, it was found that the sintered specimen of the $Ca_{65}Mg_{15}Zn_{20}$ metallic glass alloy powder produced by setting the sintering temperature in the spark plasma sintering method to 150° C. had a compressive strength lower than 300 MPa.

Further, as indicated in Comparative Example 2, it was found that the sintered specimen of the $Ca_{65}Mg_{15}Zn_{20}$ alloy powder produced by the casting method in the alloying step had an even lower compressive strength (118 MPa).

Titanium, which is considered to be a benchmark in terms of mechanical strength in the development of biodegradable medical materials, has a compressive strength of 436 MPa as indicated by Comparative Example 10.

That is, the compressive strength of the $Ca_{65}Mg_{15}Zn_{20}$ metallic glass alloy molded body (Comparative Example 2) produced by the casting method was 118 MPa, which was absolutely insufficient as the mechanical strength of a medical material, whereas the $Ca_{65}Mg_{15}Zn_{20}$ metallic glass alloy molded bodies (Examples 3 to 5) produced according to the present invention had a compressive strength close to the mechanical strength of titanium.

Incidentally, the compressive strength of polylactic acid currently being developed as a biomaterial is about 74 MPa (see NPL 3 and the like).

(Test of Making $Ca_{65}Mg_{15}Zn_{20}$ Metallic Glass Alloy Molded Body with Dispersed Fe Crystal Grains—2—)

The following test was carried out to confirm the compressive strength in the case where the step of dispersing Fe crystal grains is added between the step of alloying and the step of sintering the alloyed mixed metal powder according to the present invention.

As indicated in Examples 6 to 9 in Table 1, specimens (Examples 6 to 9) were made by making a $Ca_{65}Mg_{15}Zn_{20}$ metallic glass alloy powder by a gas atomization method, then dispersing Fe crystal grains in an amount of 5 volume % to 20 volume %, and sintering at a sintering temperature of 140° C.

For comparison, a pure titanium specimen indicated as Comparative Example 10 in Table 1 was used.

In the compression tests of the specimens of Examples 6 to 9, quadrangular prism-shaped measurement pieces having a width of 2 mm, a thickness of 2 mm, and a height of 4 mm were made, and the relationship between compressive strength and strain was measured at a constant crosshead speed corresponding to an initial strain rate of $5 \times 10^{-4}$ mm/s under uniaxial pressure by using a conventional mechanical test machine (high-temperature vacuum tensile/compression tester AG50VF, manufactured by Shimadzu Corporation).

The compression test of the specimen of Comparative Example 10 was similarly carried out by using a conventional mechanical test machine (high-temperature vacuum tensile/compression tester AG50VF, manufactured by Shimadzu Corporation) with respect to a specimen having a diameter of 1.48 mm and a height of 3.78 mm.

The compression test results are depicted in FIGS. 13A to 13D (Examples 6 to 9) and FIG. 14 (Comparative Example 10).

The compressive strength of each specimen which is determined based on the compression test results is depicted in Table 3.

TABLE 3

| | Fe volume % | Compressive strength (MPa) |
|---|---|---|
| Example 6 | 5 | 354.08 |
| Example 7 | 10 | 388.99 |
| Example 8 | 15 | 411.19 |
| Example 9 | 20 | 387.48 |
| Comparative Example 10 | — | 436.00 |

As indicated by Examples 6 to 9 in Table 3, it is understood that the compressive strength and the mechanical strength are improved by dispersing Fe crystal grains as compared with Example 5 (specimen without dispersion of Fe crystal grains) in Table 2.

Further, it is indicated that the compressive strength of the $Ca_{65}Mg_{15}Zn_{20}$ metallic glass alloy molded bodies with dispersed Fe crystal grains (Examples 6 to 9) is closer to the mechanical strength of titanium than that of the metallic glass alloy molded body which is produced by the production method of the present invention but in which Fe crystal grains have not been dispersed.

(Vickers Hardness Test)

A Vickers hardness test was carried out in the following manner with respect to the calcium-based metallic glass alloy molded body for medical use produced by the production method of the present invention.

A Micro WiZhard HM-211 type microhardness tester manufactured by Mitutoyo Corporation was used for measuring hardness of the specimens indicated in Examples 3 to 5 and Comparative Examples 4, 5, 2 and 10 in Table 1.

The results of the Vickers hardness test are depicted in Table 4.

TABLE 4

| | Sintering temperature (° C.) | Vickers hardness (HV) | |
|---|---|---|---|
| | | Average value | Standard deviation |
| Example 3 | 120 | 168.55 | 12.12 |
| Example 4 | 130 | 173.42 | 12.50 |
| Example 5 | 140 | 177.16 | 3.10 |
| Comparative Example 4 | 150 | 185.26 | 10.15 |
| Comparative Example 5 | 160 | 186.66 | 6.73 |
| Comparative Example 2 | — | 83.33 | 2.70 |
| Comparative Example 10 | — | 128.40 | 3.20 |

As shown in Table 4, it is understood that the calcium-based metallic glass alloy molded body for medical use which is produced according to the present invention is significantly harder than the benchmark titanium.

(SBF Immersion Test—1—)

An SBF immersion test was carried out in the following manner with respect to the calcium-based metallic glass alloy molded body for medical use produced by the production method of the present invention.

As indicated in Example 10 in Table 1, a $Ca_{65}Mg_{15}Zn_{20}$ metallic glass alloy powder was made by a gas atomization method, and then a $Ca_{65}Mg_{15}Zn_{20}$ metallic glass alloy molded body was made by a spark plasma sintering method. In the spark plasma sintering method, the $Ca_{65}Mg_{15}Zn_{20}$ metallic glass alloy powder of 53 μm to 150 μm was treated under the conditions set to a loading pressure of 600 MPa, a holding time of 10 min after reaching the sintering temperature, and a sintering temperature of 95° C.

The $Ca_{65}Mg_{15}Zn_{20}$ metallic glass alloy molded body of Example 10 which was molded in a mold having a diameter of 15 mm and cut was immersed in an SBF (simulated body fluid) of the abovementioned composition under the condition of 37° C., and the mass decrease of the metallic glass alloy molded body was measured to calculate the degradation rate.

Figure 15:
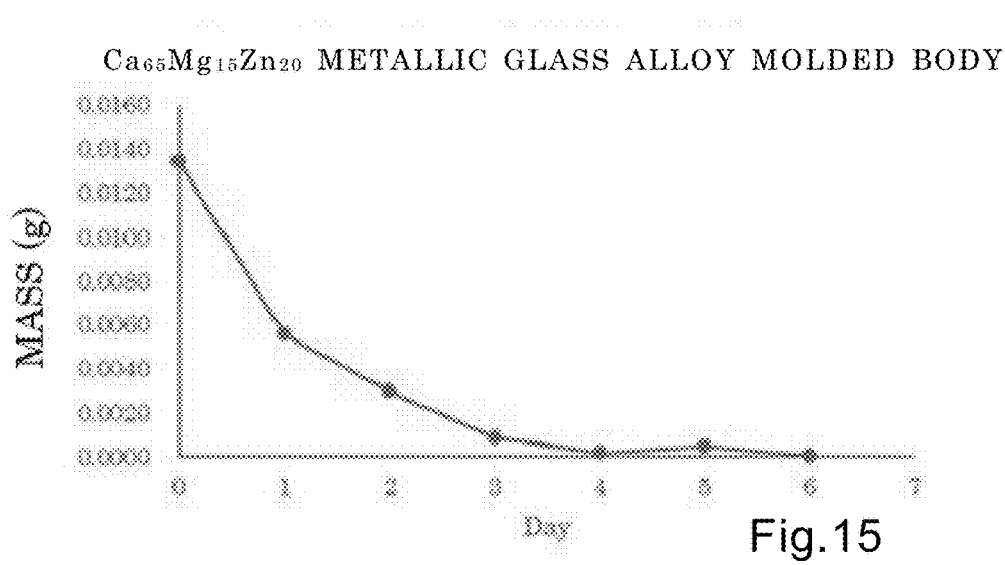
FIG. 15 depicts a simulated body fluid immersion test result (change in mass over time) of a $Ca_{65}Mg_{15}Zn_{20}$ metallic glass alloy molded body.

FIG. 15 and Table 5 depict how the mass decrease of the $Ca_{65}Mg_{15}Zn_{20}$ metallic glass alloy molded body of Example 10 changes over time.

TABLE 5

| Number of immersion days | Mass (g) | Degradation rate (mass %) |
|---|---|---|
| 0 | 0.0135 | — |
| 1 | 0.0056 | 58.5 |
| 2 | 0.0030 | 77.8 |
| 3 | 0.0009 | 93.3 |
| 4 | 0.0002 | 98.5 |
| 5 | 0.0005 | 96.3 |
| 6 | 0.0001 | 99.3 |

As shown in FIG. 15 and Table 5, in the SBF immersion test, a mass decrease of 90% or more was observed on the third day of immersion with respect to the mass at the start of immersion.

Figure 16:
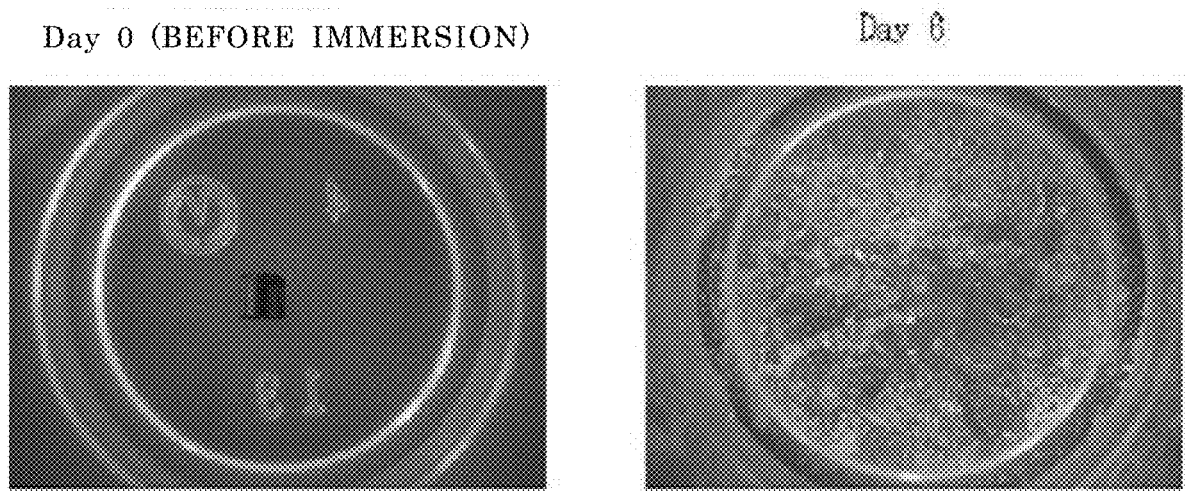
FIG. 16 depicts a simulated body fluid immersion test result (image before and after immersion) of a $Ca_{65}Mg_{15}Zn_{20}$ metallic glass alloy molded body.

Further, FIG. 16 depicted images of the $Ca_{65}Mg_{15}Zn_{20}$ metallic glass alloy molded body of Example 9 before and after the SBF immersion. It was found that substantially all of the metallic glass alloy molded body was dissolved on the sixth day of immersion.

(SBF Immersion Test—2—)

An SBF immersion test was carried out in the following manner with respect to the calcium-based metallic glass alloy molded body for medical use produced by the production method of the present invention.

As indicated in Example 5 of Table 1, a $Ca_{65}Mg_{15}Zn_{20}$ metallic glass alloy powder was made by a gas atomization method, and a $Ca_{65}Mg_{15}Zn_{20}$ metallic glass alloy molded body was then made by a spark plasma sintering method. In the spark plasma sintering method, the $Ca_{65}Mg_{15}Zn_{20}$ metallic glass alloy powder of 53 μm or less was treated under the conditions set to a loading pressure of 600 MPa, a holding time of 10 min after reaching the sintering temperature, and a sintering temperature of 140° C.

As a comparative specimen, a $Ca_{65}Mg_{15}Zn_{20}$ alloy was made by a copper mold casting method as indicated in Comparative Example 11 in Table 1.

The specimens of Example 5 and Comparative Example 11 were subjected to an SBF immersion test. A specimen molded with a mold having a diameter of 15 mm and cut by a cutting machine was immersed in an SBF by hanging on a string under a condition of 37° C., and the decrease in mass of the calcium-based metallic glass alloy molded body was measured on an hourly basis to determine the degradation rate.

Figure 17:
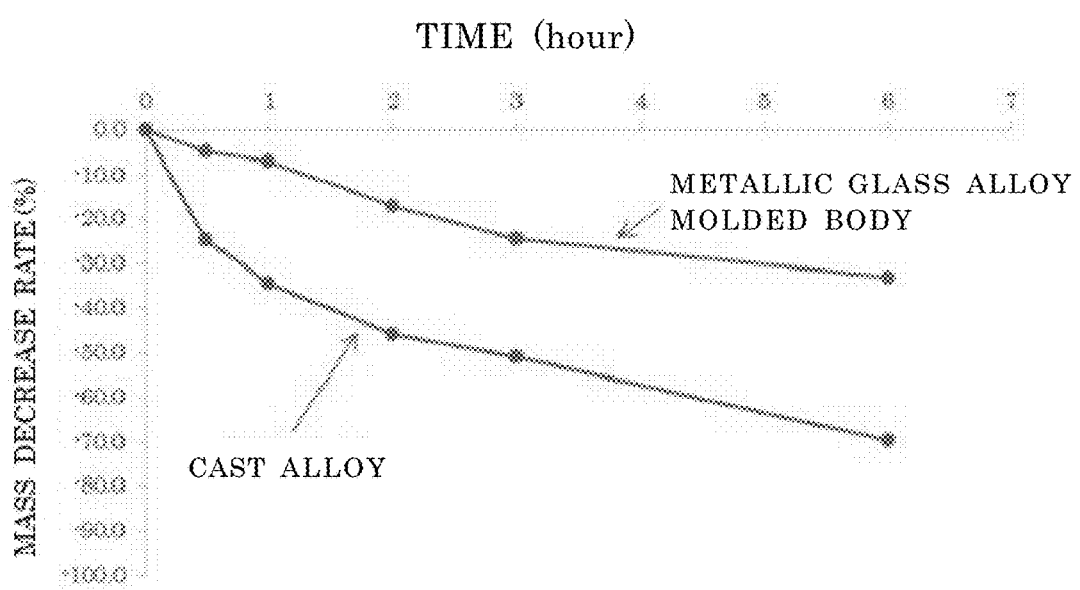
FIG. 17 depicts a simulated body fluid immersion test result (mass decrease rate over time, initial period of degradation) of a $Ca_{65}Mg_{15}Zn_{20}$ metallic glass alloy molded body.

FIG. 17 and Table 6 depict how the mass decrease rate in the SBF immersion test of the $Ca_{65}Mg_{15}Zn_{20}$ metallic glass alloy molded body of Example 5 and the $Ca_{65}Mg_{15}Zn_{20}$ cast alloy of Comparative Example 11 changes over time.

TABLE 6

| Immersion time (h) | Metallic glass alloy (example 5) Mass decrease rate (%) | Cast alloy (Comparative Example 11) Mass decrease rate (%) |
|---|---|---|
| 0 | 0 | 0 |
| 0.5 | 4.8 | 24.9 |
| 1 | 6.9 | 34.5 |
| 2 | 17.2 | 45.9 |
| 3 | 24.4 | 50.8 |
| 6 | 33.1 | 69.7 |

In the $Ca_{65}Mg_{15}Zn_{20}$ metallic glass alloy molded body (Example 5), the mass decrease at 3 h after immersion was 24% with respect to the mass at the start of immersion, and the mass decrease at 6 h after immersion was 33% with respect to the mass at the start of immersion. Meanwhile, in the $Ca_{65}Mg_{15}Zn_{20}$ cast alloy (Comparative Example 11), the mass decrease at 3 h after immersion was 51% with respect to the mass at the start of immersion, and the mass decrease at 6 h after immersion was 70% with respect to the mass at the start of immersion.

That is, it was found that the absorption of the metallic glass alloy molded body produced by the production method of the present invention proceeds more gradually as compared with the cast alloy.

(Study on Thickness of Metallic Glass Alloy Molded Body and Alloying Step)

The thickness of the metallic glass alloy molded bodies was studied by comparing the results obtained for the $Ca_{65}Mg_{15}Zn_{20}$ metallic glass alloy molded body (Example 5) made by the gas atomization method and spark plasma sintering method and the $Ca_{65}Mg_{15}Zn_{20}$ metallic glass alloy molded body (ingot, Comparative Example 2) which had the same metal composition of $Ca_{65}Mg_{15}Zn_{20}$, the same specimen diameter of 15 mm and the same specimen length of 40 mm, but was made by the casting method.

The $Ca_{65}Mg_{15}Zn_{20}$ alloy of Comparative Example 2 can be confirmed to have no properties of metal glass from the X-ray diffraction spectrum (FIG. 8), to have only a compressive strength lower than 300 MPa from the compression test results (FIG. 12), and to have a Vickers hardness which is not 120 HV or more from the Vickers hardness test results (Table 4). Thus, it is understood that this alloy is not suitable for the calcium-based metallic glass alloy molded body for medical use of the present invention.

Meanwhile, the $Ca_{65}Mg_{15}Zn_{20}$ metallic glass alloy molded body of Example 5 can be confirmed to have properties of metal glass from the X-ray diffraction spectrum (FIG. 9D), to have a compressive strength higher than 300 MPa from the compression test results (FIG. 11C), and to have a Vickers hardness which is 120 HV or more from the Vickers hardness test results (Table 4). Thus, it is understood that this molded body is suitable for the calcium-based metallic glass alloy molded body for medical use of the present invention.

In other words, it is understood that where the diameter of the columnar metallic glass alloy molded body is 15 mm or more, that is, in the case of a large lump including a region inside the molded body in which the shortest distance from all parts of the surface of the molded body is 7.5 mm or more, the casting method is not suitable for a metallic glass alloy biomaterial. The results of the present investigation are consistent with the fact that where the thickness of the specimen described in NPL 4 to 6 exceeds 10 mm, the specimens are not suitable for the metallic glass alloy biomaterial in the casting method.

INDUSTRIAL APPLICABILITY

With the production method of the present invention, it is possible to provide a calcium-based metallic glass alloy biomaterial for medical use which has a biodegradable property and mechanical strength and is suitable for a wide range of applications.

Since the calcium-based metallic glass alloy biomaterial for medical use has mechanical strength and hardness equivalent to those of metal materials, materials for medical use which have a complex shape can be molded and the alloy can be used for members to which pressure is applied due to the structure of the biomaterial or implantation position.

Further, gradual absorption of the calcium-based metallic glass alloy biomaterial for medical use, by the living body, starts immediately after the implantation in the living body, and the alloy is eventually degraded in the living body. As a result, not only the removal operation after the treatment is unnecessary, but also the degradation speed can be controlled immediately after the implantation.

By using the present invention, it is possible to design an alloy compatible with various medical devices regardless of size, such as a stent, a bone fragment fixing plate, a fixing screw, a dental membrane, and the like, by using a novel calcium-based metallic glass alloy molded body for medical use, and the present invention can be expected to be applied to various medical fields.

The invention claimed is:

1. A calcium-based metallic glass alloy molded body for medical use, wherein
    the molded body is a single, homogenous molded body consisting of a calcium-based metallic glass alloy and Fe crystal grains,
    the calcium-based metallic glass alloy includes calcium, magnesium and zinc as a calcium-based ternary metallic glass alloy material,
    a composition of the calcium in the calcium-based metallic glass alloy is 40 at. % or more and 70 at. % or less,
    a composition of the magnesium is 30 at. % or less, and
    a composition of the zinc is 35 at. % or less, and
    the single, homogenous molded body having a thickness of 15 mm or more from all parts of any surface of the single, homogenous molded body,
    wherein the single, homogenous molded body comprises metallic glass properties in a pre-sintered state and a post-sintered state of the calcium-based metallic glass alloy and Fe crystal grains,
    wherein the Fe of the single, homogenous molded body has a purity of 99% or more.

2. The calcium-based metallic glass alloy molded body for medical use according to claim 1, wherein the single, homogenous molded body further includes 5 volume % to 30 volume % of Fe crystal grains.

3. The calcium-based metallic glass alloy molded body for medical use according to claim 1, wherein a compressive strength is 300 MPa or more.

4. The calcium-based metallic glass alloy molded body for medical use according to claim 1, wherein a Vickers hardness is 120 HV or more.

5. The calcium-based metallic glass alloy molded body for medical use according to claim 1, wherein, in a simulated body fluid immersion test, a decomposition rate in immersion for 3 days is 90 mass % or more, wherein the single, homogenous molded body is immersed in an simulated body fluid under the condition of 37° C., wherein the simulated body fluid comprises 8.035 g of NaCl, 0.355 g of $NaHCO_3$, 0.225 g of KCl, 0.231 g of K$_2$HPO$_4$.3H$_2$O, 0.311 g of MgCl$_2$.6H$_2$O, 39 ml of 1.0M HCl, 0.292 g of CaCl$_2$, 0.072 g of NaSO$_4$, and 6.118 g of Tris.

6. The calcium-based metallic glass alloy molded body for medical use according to claim 1, wherein, in a simulated body fluid immersion test, a degradation rate in immersion for 5 hours is 30 mass % or less, wherein the single, homogenous molded body is immersed in an simulated body fluid under the condition of 37° C., wherein the simulated body fluid comprises 8.035 g of NaCl, 0.355 g of NaHCO$_3$, 0.225 g of KCl, 0.231 g of K$_2$HPO$_4$.3H$_2$O, 0.311 g of MgCl$_2$.6H$_2$O, 39 ml of 1.0M HCl, 0.292 g of CaCl$_2$, 0.072 g of NaSO$_4$, and 6.118 g of Tris.

7. A calcium-based metallic glass alloy biomaterial for medical use constituted of the calcium-based metallic glass alloy molded body for medical use according to claim 1.

8. A production method of a calcium-based metallic glass alloy molded for medical use body according to claim 1, the method comprising:
 a mixing step of a metal powder including a calcium powder;
 an alloying step of the mixed metal powder; and
 a sintering step of the alloyed mixed metal powder,
 wherein the calcium-based metallic glass alloy includes calcium, magnesium and zinc as a calcium-based ternary metallic glass alloy material, and
 wherein a composition of the calcium in the calcium-based metallic glass alloy is 40 at. % or more and 70 at. % or less, a composition of the magnesium is 30 at. % or less, and a composition of the zinc is 35 at. % or less.

9. The production method of a calcium-based metallic glass alloy molded body for medical use according to claim 8, wherein the alloying step is a gas atomization method.

10. The production method of a calcium-based metallic glass alloy molded body for medical use according to claim 8, wherein the alloying step is a mechanical alloying method.

11. The production method of a calcium-based metallic glass alloy molded body for medical use according to claim 8, wherein
 the alloying step includes:
 an obtaining step of an ingot from the mixed metal powder by a casting method; and
 an alloying step of the ingot by a mechanical alloying method.

12. The production method of a calcium-based metallic glass alloy molded body for medical use according to claim 8, wherein the sintering step is a spark plasma sintering method.

13. The production method of a calcium-based metallic glass alloy molded body for medical use according to claim 12, wherein the spark plasma sintering method is performed under conditions of a loading pressure of 10 MPa to 800 MPa, a holding time after reaching a sintering temperature of 0 min to 20 min, and a sintering temperature of 85° C. to 145° C.

14. The production method of a calcium-based metallic glass alloy molded body for medical use according to claim 10, the method further including a dispersing step of iron crystal grains between the alloying step and the sintering step of the alloyed mixed metal powder.

15. A production method of a calcium-based metallic glass alloy biomaterial for medical use, the method including a machining step of the calcium-based metallic glass alloy molded body for medical use according to claim 1.

16. A calcium-based metallic glass alloy biomaterial for medical use constituted of the calcium-based metallic glass alloy molded body for medical use according to claim 2.

17. A calcium-based metallic glass alloy molded body for medical use, wherein
 the molded body is a single, homogenous molded body consisting of a calcium-based metallic glass alloy including calcium as a main component,
 the calcium-based metallic glass alloy includes calcium, magnesium and zinc as a calcium-based ternary metallic glass alloy material,
 a composition of the calcium in the calcium-based metallic glass alloy is 40 at. % or more and 70 at. % or less,
 a composition of the magnesium is 30 at. % or less, and
 a composition of the zinc is 35 at. % or less, and
 the single, homogenous molded body having a thickness of 15 mm or more from all parts of any surface of the single, homogenous molded body,
 wherein the single, homogenous molded body comprises metallic glass properties in a pre-sintered stated and a post-sintered state of the calcium-based metallic glass alloy,
 wherein each of the calcium, magnesium and zinc of the single, homogenous molded body has a purity of 99% or more.

18. The calcium-based metallic glass alloy molded body for medical use according to claim 17, wherein a compressive strength is 300 MPa or more.

19. The calcium-based metallic glass alloy molded body for medical use according to claim 17, wherein a Vickers hardness is 120 HV or more.

20. The calcium-based metallic glass alloy molded body for medical use according to claim 17, wherein, in a simulated body fluid immersion test, a decomposition rate in immersion for 3 days is 90 mass% or more, wherein the single, homogenous molded body is immersed in an simulated body fluid under the condition of 37° C., wherein the simulated body fluid comprises 8.035 g of NaCl, 0.355 g of NaHCO$_3$, 0.225 g of KCl, 0.231 g of K$_2$HPO$_4$.3H$_2$O, 0.311 g of MgCl$_2$.6H$_2$O, 39 ml of 1.0M HCl, 0.292 g of CaCl$_2$, 0.072 g of NaSO$_4$, and 6.118 g of Tris.

21. The calcium-based metallic glass alloy molded body for medical use according to claim 17, wherein, in a simulated body fluid immersion test, a degradation rate in immersion for 5 hours is 30 mass % or less, wherein the single, homogenous molded body is immersed in an simulated body fluid under the condition of 37° C., wherein the simulated body fluid comprises 8.035 g of NaCl, 0.355 g of NaHCO$_3$, 0.225 g of KCl, 0.231 g of K$_2$HPO$_4$.3H$_2$O, 0.311 g of MgCl$_2$.6H$_2$O, 39 ml of 1.0M HCl, 0.292 g of CaCl$_2$, 0.072 g of NaSO$_4$, and 6.118 g of Tris.

22. A calcium-based metallic glass alloy biomaterial for medical use constituted of the calcium-based metallic glass alloy molded body for medical use according to claim 17.

* * * * *